United States Patent
Broderick et al.

(10) Patent No.: US 11,590,175 B2
(45) Date of Patent: *Feb. 28, 2023

(54) COMPOSITIONS CONTAINING AMNIOTIC COMPONENTS AND METHODS FOR PREPARATION AND USE THEREOF

(71) Applicant: MERAKRIS THERAPEUTICS INC., Research Triangle Park, NC (US)

(72) Inventors: Thomas Christopher Broderick, Hillsborough, NC (US); William Samuel Fagg, IV, Galveston, TX (US)

(73) Assignee: MERAKRIS THERAPEUTICS LLC, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/640,699

(22) PCT Filed: Aug. 23, 2018

(86) PCT No.: PCT/US2018/047818
§ 371 (c)(1),
(2) Date: Feb. 20, 2020

(87) PCT Pub. No.: WO2019/040790
PCT Pub. Date: Feb. 28, 2019

(65) Prior Publication Data
US 2020/0352848 A1    Nov. 12, 2020

Related U.S. Application Data

(60) Provisional application No. 62/549,076, filed on Aug. 23, 2017.

(51) Int. Cl.
| | | |
|---|---|---|
| *A61K 35/50* | (2015.01) | |
| *A61P 17/02* | (2006.01) | |
| *A01N 1/02* | (2006.01) | |
| *A61K 8/67* | (2006.01) | |
| *A61K 8/98* | (2006.01) | |
| *A61K 9/00* | (2006.01) | |
| *A61K 31/355* | (2006.01) | |
| *A61K 31/455* | (2006.01) | |
| *A61K 35/51* | (2015.01) | |
| *A61L 27/36* | (2006.01) | |
| *A61L 27/54* | (2006.01) | |
| *A61Q 19/00* | (2006.01) | |
| *A61Q 19/08* | (2006.01) | |
| *C12N 5/073* | (2010.01) | |
| *C12N 5/0775* | (2010.01) | |
| *A61K 8/99* | (2017.01) | |
| *A01N 63/10* | (2020.01) | |

(52) U.S. Cl.
CPC ........... *A61K 35/50* (2013.01); *A01N 1/0226* (2013.01); *A01N 63/10* (2020.01); *A61K 8/675* (2013.01); *A61K 8/678* (2013.01); *A61K 8/982* (2013.01); *A61K 8/99* (2013.01); *A61K 9/0014* (2013.01); *A61K 31/355* (2013.01); *A61K 31/455* (2013.01); *A61K 35/51* (2013.01); *A61L 27/3604* (2013.01); *A61L 27/3683* (2013.01); *A61L 27/54* (2013.01); *A61P 17/02* (2018.01); *A61Q 19/00* (2013.01); *A61Q 19/007* (2013.01); *A61Q 19/08* (2013.01); *C12N 5/0605* (2013.01); *C12N 5/0665* (2013.01); *A61K 2800/10* (2013.01); *A61K 2800/522* (2013.01); *A61K 2800/805* (2013.01); *C12N 2501/999* (2013.01); *C12N 2506/025* (2013.01)

(58) Field of Classification Search
CPC ........ A61K 35/50; A61K 8/675; A61K 8/678; A61K 8/99; A61P 17/02; A01N 63/10
See application file for complete search history.

(56) References Cited

U.S. PATENT DOCUMENTS

| | | | |
|---|---|---|---|
| 4,496,086 A | | 1/1985 | Duchadeau |
| 4,798,824 A | | 1/1989 | Belzer et al. |
| 5,152,456 A | | 10/1992 | Ross et al. |
| 5,261,601 A | | 11/1993 | Ross et al. |
| 5,280,784 A | | 1/1994 | Kohler |
| 5,309,900 A | | 5/1994 | Knoch et al. |
| 5,312,046 A | | 5/1994 | Knoch et al. |

(Continued)

FOREIGN PATENT DOCUMENTS

| | | |
|---|---|---|
| CA | 2543528 A1 | 5/2005 |
| CN | 105039244 A * | 11/2015 |

(Continued)

OTHER PUBLICATIONS

Rouiller et al. (MAbs. May-Jun. 2013;5(3):501-11) (Year: 2013).*
Rathbone et al. (J Orthop Res. Jul. 2011;29(7):1070-4.) (Year: 2011).*
Souza et al. (Genetics and Molecular Biology [online], 2004, v. 27, n. 3 [Accessed May 31, 2021], pp. 454-459.) (Year: 2004).*

(Continued)

*Primary Examiner* — Mark V Stevens
(74) *Attorney, Agent, or Firm* — McCarter & English, LLP; Beverly W. Lubit

(57) ABSTRACT

Compositions are provided that contain biologically active components of amniotic fluid including growth factors and other proteins, carbohydrates, lipids, and metabolites. The compositions containing biologically active components of amniotic fluid can be useful for a range of therapeutic treatments including joint and soft tissue repair, regulation of skin condition, and for use in organ preservation, such as for use in organ transplant procedures. Advantages of the compositions include that they can be reproducibly produced, without the inherent variability of amniotic fluid from individual donors, and that they are free of fetal waste.

20 Claims, 9 Drawing Sheets

(56) References Cited

U.S. PATENT DOCUMENTS

| | | | |
|---|---|---|---|
| 5,458,136 A | 10/1995 | Jaser et al. | |
| 5,461,695 A | 10/1995 | Knoch | |
| 5,518,179 A | 5/1996 | Humberstone et al. | |
| 5,549,102 A | 8/1996 | Lintl et al. | |
| 5,552,267 A | 9/1996 | Stern et al. | |
| 5,740,966 A | 4/1998 | Blaha-Schnabel | |
| 5,957,389 A | 9/1999 | Wunderlich et al. | |
| 6,000,394 A | 12/1999 | Blaha-Schnabel et al. | |
| 6,085,741 A | 7/2000 | Becker | |
| 6,106,479 A | 8/2000 | Wunderlich et al. | |
| 6,176,237 B1 | 1/2001 | Wunderlich et al. | |
| 6,513,519 B2 | 2/2003 | Gallem | |
| 6,513,727 B1 | 2/2003 | Jaser et al. | |
| 6,962,151 B1 | 11/2005 | Knoch et al. | |
| 6,983,747 B2 | 1/2006 | Gallem et al. | |
| 7,059,320 B2 | 6/2006 | Feiner et al. | |
| 7,252,085 B2 | 8/2007 | Kunschir | |
| 8,551,538 B2 | 10/2013 | Qian | |
| 9,132,156 B1 | 9/2015 | Werber et al. | |
| 9,220,631 B2 | 12/2015 | Sigg et al. | |
| 9,579,350 B1 | 2/2017 | Harrell | |
| 2001/0003586 A1 | 6/2001 | Vatter et al. | |
| 2003/0211604 A1 | 11/2003 | E. Brown | |
| 2004/0081681 A1 | 4/2004 | Vromen | |
| 2005/0118712 A1 | 6/2005 | Tsai et al. | |
| 2007/0207127 A1 | 9/2007 | Kato et al. | |
| 2007/0292401 A1 | 12/2007 | Harmon et al. | |
| 2010/0317104 A1* | 12/2010 | Elefanty | C12N 5/0606 435/366 |
| 2012/0141399 A1* | 6/2012 | You | A61Q 17/04 424/62 |
| 2013/0183387 A1* | 7/2013 | Palladino | A61K 31/56 424/582 |
| 2014/0050706 A1 | 2/2014 | Shroff | |
| 2014/0336600 A1 | 11/2014 | Harrell | |
| 2015/0050251 A1 | 2/2015 | Trumpower et al. | |
| 2015/0140114 A1 | 5/2015 | Sasko | |
| 2016/0022744 A1 | 1/2016 | Burt | |
| 2016/0287752 A1 | 10/2016 | Britt | |
| 2016/0310534 A1* | 10/2016 | Chang | A61P 25/00 |
| 2016/0375064 A1 | 12/2016 | Beaudry et al. | |
| 2017/0042943 A1 | 2/2017 | Namin et al. | |
| 2018/0000869 A1 | 1/2018 | Britt | |
| 2019/0300848 A1 | 10/2019 | Fagg et al. | |

FOREIGN PATENT DOCUMENTS

| | | | |
|---|---|---|---|
| CN | 105039244 A | 11/2015 | |
| EP | 2046946 A2 | 4/2009 | |
| WO | 2008/036447 A2 | 3/2008 | |
| WO | 2013/082487 A1 | 6/2013 | |
| WO | 2017/003954 A1 | 1/2017 | |
| WO | WO-2017023690 A1 * | 2/2017 | A61K 35/545 |

OTHER PUBLICATIONS

Chen, Q , et al. Human amniotic epithelial cell feeder layers maintain iPS cell pluripotency by inhibiting endogenous DNA methyltransferase 1. Experimental and therapeutic medicine 6: 1145-1154, 2013.

Buseman, J.,et al. Amniotic Fluid for Ex Vivo Skin Preservation: A Comparative Study of Tissue Preservation Solutions. Annals of Plastic Surgery: Dec. 2013—vol. 71—Issue 6—p. 643-645.

Abraham, J. and Klagsburn, M. Modulation of Wound Repair by Members of the Fibroblast Growth Factor family. In Clark, R. Ed. The molecular and cellular biology of wound repair. 2nd Ed. New York, Plenum Press, pp. 195-248 (1996).

Aggarwal, BB, Signalling Pathways of the TNF Superfamily: a Double-Edged Sword. Nature Revs. Immuno. (2003) 3:745-56.

Alonso JE et al., The management of complex orthopedic injuries. Surg Clin North Am 1996; 76: 879-903.

Bakhtyar, N., et al. Exosomes from acellular Wharton's jelly of the human umbilical cord promotes skin wound healing. Stem Cell Research & Therapy (2018) 9:193.

Baulier, E. et al. Amniotic Fluid-Derived Mesenchymal Stem Cells Prevent Fibrosis and Preserve Renal Function in a Preclinical Porcine Model of Kidney Transplantation Stem Cells Translational Medicine. 2014;3:809-820.

Benirschke, K. and Kaufmann, P. Pathology of the human placenta. 4th Ed. New York, Springer-Verlag, 2000, pp. 42-46, 116, 281-297.

Benirschke, K. and Kaufmann, P. Pathology of the human placenta. New York, Springer-Verlag, 2000, 42-46, 116, 281-297.

Bigbey, M., eta al. Amnion-Derived Fluid and Amniotic Fluid. Axolotl Biologix. MRK0001-V 1.0.0. 2 pages.

Brooks, P. et al., Requirement of vascular integrin alpha v beta 3 for angiogenesis. Science, 264, 569-571 (1994).

Brown, E. Phagocytosis, Bioessays, 17:109-117 (1995).

Brown, L. et al. Expression of vasclar permeability factor (vascular endothelial growth factor) by epidermal keratinocytes during wound healing. J Exp Med, 176, 1375-1379 (1992).

Bugge, T. et al., Loss of fibrinogen rescues mice from the pleiotropic effects of plasminogen deficiency. Cell, 87, 709-719 (1996).

Camilli, T. C., Striking the Target in Wnt-y Conditions: Intervening in Wnt Signaling During Cancer Progression. Biochem. 2010, Pharmacol. 80(5): 702-711.

Campbell, J. et al., "Biochemical composition of amniotic fluid and extrambryonic coelomic fluid in the first trimester of pregnancy," Br. J. Obstet. Gynaecol. (1992) 99 (7): 563-565.

Carreira-Barbosa F, et al., Prickle 1 regulates cell movements during gastrulation and neuronal migration in zebrafish. Development 2003, 130(17):4037-4046.

Casey, M. and MacDonald P. Interstitial Collagen Synthesis and Processing in Human Amnion: A Property of the Mesenchymal Cells. Biol Reprod, 1996, 55: 1253-1260.

Chan-Kyung, J., et al. Proteomics Analysis of Human Amniotic Fluid. Molecular & Cellular Proteomics 6:1406-1415, 2007.

Chang, L. et al. The dynamic properties of intermediate filaments during organelle transport. Journal of Cell Science 122, 2914-2923 (2009).

Cho, C-K.J., et al., "Proteomics Analysis of Human Amniotic Fluid," (2007) Molecular & Cellular Proteomics 6: 1406-1415.

Ciubotaru, A. and Haverrich, A., Ex vivo Approach to Treat Failing Organs: Expanding the Limits. Eur. Surg. Res. (2015) 54: 64-74.

Clark R. et al., Fibronectin and Fibrin Provide a Provisional Matrix for Epidermal Cell Migration During Wound Reepithelialization. J. Invest Dermatol, 79, pp. 264-269 (1982).

Clark, R. et al., Collagen matrices attenuate the collagen-synthetic response of cultured fibroblasts to TGF-β. J Cell Sci, 108, pp. 1251-1261 (1995).

Clark, R. et al., Fibronectin is produced by blood vessels in response to injury. J. Exp Med, 156, 646-651 (1982).

Clark, R. et al., Platelet isoforms of platelet-derived growth factor stimulate fibroblasts to contract collagen matrices. J Clin Invest, 84, 1036-1040 (1989).

Clark, R., Fibronectin Matrix Deposition and Fibronectin Receptor Expression in Healing and Normal Skin. J Invest Dermatol, 94, Suppl, pp. 128S-134S (1990).

Collins, GM et al, Kidney preservation for transportation experimental analysis of optimal perfusate composition. Br. J. Surg. (1972) 59: 187-89.

Courtman, DW et al.,Development of a pericardial acellular matrix biomaterial: biochemical and mechanical effects of cell extraction. J Biomed Mater Res 1994; 28:655-666.

Coutinho, P., et al. Limiting burn extension by transient inhibition of connexin 43 expression at the site of injury. Br J Plast Surg 58, 658-67 (2005).

Cunningham, F. et al., The placenta and fetal membranes, Williams Obstetrics, 20th ed. Appleton and Lange, 1997, 95-125.

Davydova, DA., et al. Cell Phenotypes in Human Amniotic Fluid. Acta Naturae. No. 2. 2009. pp. 98-103.

Desmouliere, A. and Gabbiani, G. The role of the myofibroblast in wound healing and fibrocontractive diseases. In Clark, R. Ed. The molecular and cellular biology of wound repair. 2nd Ed. New York, Plenum Press, Chapter 13 pp. 391-423 (1996).

Eslaminejad, MB., et al. Amniotic Fluid Stem Cells and Their Application in Cell-Based Tissue Regeneration. Int J Fertil Steril. 2012; 6(3): 147-156.

(56) References Cited

OTHER PUBLICATIONS

Folkman, J. and D'Amore, P, Blood Vessel Formation: What Is Its Molecular Basis?. Cell, 87, pp. 1153-1155 (1996).

Folkman, J., Angiogenesis and angiogenesis inhibition: an overview, EXS, 79, 1-8, (1997).

Fundamental Immunology, 4th Ed., William E. Paul, ed. Lippincott-Raven Publishers, Philadelphia (1999) at 1051-1053.

Gabbiani, G. et al., Cytoplasmic filaments and gap junctions in epithelial cells and myofibroblasts during wound healing. J Cell Biol, 76, pp. 561-568 (1978).

Gao X et al., Effects of amniotic fluid on proteases: a possible role of amniotic fluid in fetal wound healing. Ann Plastic Surg 1994; 33: 128-134.

Goliger, J. and Paul, D. Wounding alters epidermal connexin expression and gap junction-mediated intercellular communication. Mol Biol Cell, 6, pp. 1491-1501 (1995).

Gordon, MD and Nusse, R. Wnt Signaling: Multiple Pathways, Multiple Receptors, and Multiple Transcription Factors. J. Biol. Chem. (2006) 281 (32) 22429-22433.

Gorentla, BK and Zhong, X-P, T Cell receptor signal transduction in T Lymphocytes, J. Clin. Cell Immunol. (2012) (Suppl 12) 23 pages.

Gray, A. et al., A alpha and B beta chains of fibrinogen stimulate proliferation of human fibroblasts. J Cell Sci,104, pp. 409-413 (1993).

Greiling, D. and Clark R., Fibronectin provides a conduit for fibroblast transmigration from collagenous stroma into fibrin clot provisional matrix. J. Cell Sci, 110, pp. 861-870 (1997).

Grose, R. and Werner, S. (2004). Wound-healing studies in transgenic and knockout mice. Mol Biotechnol 28, 147-66.

Grzywocz, Z. et al. Growth factors and their receptors derived from human amniotic cells in vitro. Folia Histochemica et Cytobiologica (2014) 52 (3):163-70.

Guibert, E.E. et al., Organ Preservation: Current Concepts and New Strategies for the Next Decade. Transfus. Med. Hemother. (2011) 38(2): 125-142.

Guidance for Industry: Chronic Obstructive Pulmonary Disease: Developing Drugs for Treatment. Nov. 2007. http://www.fda.gov/cder/guidance/index.htm.

Gulbis, B, et al. Amniotic fluid biochemistry in second-trimester trisomic pregnancies: relationships to fetal organ maturation and dysfunction. Early Human Development 52 (1998) 211-219.

Gupta, A. et al. (2015) Amnion and Chorion Membranes: Potential Stem Cell Reservoir with Wide Applications in Periodontics. International Journal of Biomaterials vol. 2015, Article ID 274082, 9 pages.

Heidari, Z. et al. Characterization of the Growth Factor Activity of Amniotic Fluid on Cells from Hematopoietic and Lymphoid Organs of Different Life Stages. Microbiol. Immunol., 40(8), 583-589, 1996.

Heldin, C. and Westermark B., In: Clark R., ed. The molecular and cellular biology of wound repair, 2nd Ed. New York, Plenum Press, Chapter 7. pp. 249-273, (1996).

Rouiller, et al. (2013) A high-throughput media design approach for high performance mammalian fed-batch cultures, mAbs, 5:3, 501-511.

Rathbone, et al. Effect of Various Concentrations of Antibiotics on Osteogenic CellViability and Activity. J Orthop Res 29:1070-1074, 2011.

Souza, et al. Effect of amikacin, cephalothin, clindamycin and vancomycin on in vitro fibroblast growth. Genetics and Molecular Biology, 27, 3, 454-459 (2004).

Hu, Y., et al. Exosomes from human umbilical cord blood accelerate cutaneous wound healing through miR-21-3p-mediated promotion of angiogenesis and fibroblast function. Theranostics 2018, vol. 8, Issue 1. 169-184.

Ilan, N. et al., Distinct signal transduction pathways are utilized during the tube formation and survival phases of in vitro angiogenesis. J Cell Sci, 111, 3621-3631 (1998).

Kim, EY, et al. The potential of mesenchymal stem cells derived from amniotic membrane and amniotic fluid for neuronal regenerative therapy. BMB Rep. 2014; 47(3): 135-140.

Koizumi, N., et al. Growth factor mRNA and protein in preserved human amniotic membrane. Current Eye Research. 2000, vol. 20, No. 3, pp. 173-177.

Kumar, V., et al. Animal Models for the Evaluation of Wound Healing Activity. International Bulletin of Drug Research., 3(5): 93-107, 2013.

Leibovich, S, and Ross, R., The role of the macrophage in wound repair. A study with hydrocortisone and antimacrophage serum. Am J Pathol, 78, pp. 1-100 (1975).

Lichtenberger, BM, et al. Epidermal [beta]-catenin activation remodels the dermis via paracrine signalling to distinct fibroblast lineages. Nat Commun. Feb. 3, 2016;7:10537. doi: 10.1038/ncomms10537.

Madlener, M. et al., Matrix Metalloproteinases (MMPs) and Their Physiological Inhibitors (TIMPs) Are Differentially Expressed during Excisional Skin Wound Repair. Exp Cell Res, 242, 201-210, Article No. EX984049 (1998).

Madri, J. et al., Angiogenesis in Clark, R. Ed. The molecular and cellular biology of wound repair. 2nd Ed. New York, Plenum Press, pp. 355-371 (1996).

Malone, JM et al., Detergent-extracted small-diameter vascular prostheses. J Vasc Surg 1984; 1 :181-91.

Maurer, E. J., et al., Comparison of UW and Collins solution for preservation of the rat heart. Transplantation Proceedings, (1990), vol. 22, No. 2, pp. 548-550.

Mignatti, P. et al., Proteinases and Tissue Remodeling. In Clark, R. Ed. The molecular and cellular biology of wound repair. 2nd Ed. New York, Plenum Press, 427-474 (1996).

Miki, T. Amnion-derived stem cells: in quest of clinical applications. Stem Cell Research & Therapy 2011, 2:25.

Miki, T. et al., Amnion-Derived Pluripotent/Multipotent Stem Cells. Stem Cell Reviews, 2006, 2: 133-142.

Miki, T. et al., Stem Cell Characteristics of Amniotic Epithelial Cells. Stem Cells, 2005, 23: 1549-1559.

Miyagi C, et al., STAT3 noncell-autonomously controls planar cell polarity during zebrafish convergence and extension. J Cell Biol 2004, 166(7):975-981.

Montesano, R. and Orci, L. Transforming growth factor f3 stimulates collagen-matrix contraction by fibroblasts: Implications for wound healing. Proc Natl Acad Sci USA, 85, 4894-4897 (1988).

Nanney, L. and King, L. Epidermal Growth Factor and Transforming Growth Factor-alpha. In Clark, R. Ed. The molecular and cellular biology of wound repair. 2nd Ed. New York, Plenum Press, pp. 171-194 (1996).

Nissen, N. et al., Vascular endothelial growth factor mediates angiogenic activity during the proliferative phase of wound healing. Am J Pathol, 152, 1445-1552 (1998).

Oliveira, MS, et al. Placental-derived stem cells: Culture, differentiation and challenges. World J Stem Cells, May 26, 2015; 7(4): 769-775.

Orczyk-Pawilowicz, M., et al., "Metabolomics of human amniotic fluid and maternal plasma during normal pregnancy," PLos ONE (2016) 11(4): e0152740.

Ozgenel G Y et al., Effects of human amniotic fluid on peripheral nerve scarring and regeneration in rats. J Neurosurg 2003; 98: 371-377.

Paladini, R. et al., Onset of re-epithelialization after skin injury correlates with a reorganization of keratin filaments in wound edge keratinocytes: defining a potential role for keratin 16. J. Cell Biol, 132, pp. 381-397 (1996).

Parolini, O. et al., Concise Review: Isolation and Characterization of Cells from Human Term Placenta: Outcome of the First International Workshop on Placenta Derived Stem Cells. Stem Cell, 2008, 26:300-311.

Pilcher, B. et al., The activity of collagenase-1 is required for keratinocyte migration on a type I collagen matrix. J Cell Biol, 137, pp. 1445-1457 (1997).

Pintucci, G. et al., Angiogenesis and the Fibrinolytic System. Semin Thromb Hemost, 22, 517-524 (1996).

Qian D, et al., Wnt5a functions in planar cell polarity regulation in mice. Dev Biol 2007, 306(1):121-133.

(56) References Cited

OTHER PUBLICATIONS

Qiu, C, et al. Targeting connexin 43 expression accelerates the rate of wound repair. Curr Biol 13, 1697-703 (2003).

Rappolee, D. et al., Wound macrophages express TGF-alpha and other growth factors in vivo: analysis by mRNA phenotyping. Science, 241, pp. 708-712 (1988).

Rennie, K. et al., "Applications of amniotic membrane and fluid in stem cell biology and regenerative medicine," Stem Cells Intl. (2012) Article ID 721538, 13 pages.

Riches, D., In Clark R., Ed. The molecular and cellular biology of wound repair, 2nd Ed. New York, Plenum Press, Chapter 3 pp. 95-141. 1988.

Roberts, A. and Sporn, M, Transforming Growth Factor-beta. Clark, R. ed. The molecular and cellular biology of wound repair. 2nd Ed. New York, Plenum Press, pp. 275-308 (1996).

Robson MC et al., Wound healing: Biologic features and approaches to maximize healing trajectories. Curr Probl Surg 2001; 38: 72-140.

Robson, M. et al., Platelet-derived growth factor BB for the treatment of chronic pressure ulcers. Lancet, 339, pp. 23-25 (1992).

Robson, M. et al., The safety and effect of topically applied recombinant basic fibroblast growth factor on the healing of chronic pressure sores. Ann Surg, 216, pp. 401-406 (1992).

Roubelakis, MG, et al., Amniotic fluid and amniotic membrane stem cells: marker discovery, Stem Cells Intl (2012) article 107836.

Schiro, J. et al., Integrin alpha 2 beta 1 (VLA-2) mediates reorganization and contraction of collagen matrices by human cells. Cell, 67, 403-410 (1991).

Semenov, M. V.; Snapshot: Noncanonical Wnt Signaling Pathways. Cell 2007, 131: 1378.

Sephel, G.C. and Woodward, S.C. Repair, Regeneration and Fibrosis. Rubin's Pathology, Chapter 3. Rubin, R. and Strayer, D.S. Eds; 5th Ed., Wolters Kluwyer Health, /Lippincott Williams & Wilkins, Philadelphia, PA (2008), at 71.

Shao-Cong Sun, Non-canonical NF-kB signaling pathway, Cell Res. (2011) 21: 71-85.

Siar C H, et al. Differential expression of canonical and non-canonical Wnt ligands in ameloblastoma. J. Oral Pathol. Med., 2012, 41(4):332-339.

Singer AF and Clark RA, Cutaneous Wound Healing. N Engl J Med Sep. 2, 1999; 341(10): 738-746.

Soncini, M. et al., Isolation and characterization of mesenchymal cells from human fetal membranes. J Tissue Eng Regen Med, 2007, 1:296-305.

Southard, James H. and Belzer, Folkert O., Organ Preservation. Annual Review of Medicine. (1995) 46: 235-47.

Steed, D., Clinical evaluation of recombinant human platelet—derived growth factor for the treatment of lower extremity diabetic ulcers. J Vasc Surg, 21, pp. 71-78 (1995).

Sun, Shao-Cong, Non-canonical NF-kB signaling pathway, Cell Res. (2011) 21: 71-85.

Swanson, D. K., et al., Improved heart preservation with UW preservation solution. Journal of Heart Transplantation, (1988), vol. 7, No. 6, pp. 456-467.

Takeuchi M, et al., The prickle-Related Gene in Vertebrates Is Essential for Gastrulation Cell Movements. Curr Biol 2003, 13(8):674-679.

Vaalamo, M. et al., Distinct Populations of Stromal Cells Express Collagenase-3 (MMP-13) and Collagenase-1 (MMP-1) in Chronic Ulcers but Not in Normally Healing Wounds. J Invest Dermatol, 109, pp. 96-101 (1997).

Van Raemdonck, D. et al., Machine perfusion in organ transplantation: a tool for ex-vivo graft conditioning with mesenchymal stem cells?. Curr. Opin. Organ Transplant. (2013) 18: 24-33.

Velnar T et al., The Wound Healing Process: an Overview of the Cellular and Molecular Mechanisms. The Journal of International Medical Research 2009; 37: 1528-1542.

Wang Y. Wnt/Planar cell polarity signaling: A new paradigm for cancer therapy. Mol Cancer Ther, 2009; 8 (8):2103-2109.

Wei, C. J., et al. Connexins and cell signaling development and disease. (2004) Annu Rev Cell Dev Biol 20, 811-38.

Welch, M. et al., Temporal relationships of F-actin bundle formation, collagen and fibronectin matrix assembly, and fibronectin receptor expression to wound contraction.. J. Cell Biol, 110, pp. 133-145 (1990).

Werber, B., et al. A Prospective Study of 20 Foot and Ankle Wounds Treated with Cryopreserved Amniotic Membrane and Fluid Allograft. The Journal of Foot & Ankle Surgery. vol. 52, Issue 5, Sep.-Oct. 2013, pp. 615-621.

Werner, S. et al., The function of KGF in morphogenesis of epithelium and reepithelialization of wounds. Science, 266, pp. 819-822 (1994).

Weyrich AS and Zimmerman GA, Platelets: signaling cells in the immune continuum. Trends Immunol Sep. 2004; 25(9): 489-495.

Wilson, GJ et al., Acellular matrix allograft small caliber vascular prostheses. Trans Am Soc Artif Intern 1990; 36:340-343.

Woodley, D. et al., Collagen telopeptides (cross-linking sites) play a role in collagen gel lattice contraction. J Invest Dermatol, 97, 580-585 (1991).

Wu, M., et al. Comparison of the Biological Characteristics of Mesenchymal Stem Cells Derived from the Human Placenta and Umbilical Cord. Scientific Reports | (2018) 8:5014. DOI:10.1038/s41598-018-23396-1.

Xu, J. and Clark, R., Extracellular matrix alters PDGF regulation of fibroblast integrins.. J Cell Biol, 132, pp. 239-249 (1996).

Yao, T, et al. Animal-cell culture media: History, characteristics, and current issues. Reprod Med Biol. 2017;16:99-117.

Zhang, X., et al., Mesenchymal progenitor cells derived from chorionic villi of human placenta for cartilage tissue engineering. Biochem Biophys Res Commun, 2006, 340: 944-952.

Zhang, X., et al., Successful immortalization of mesenchymal progenitor cells derived from human placenta and the differentiation abilities of immortalized cells. Biochem Biophys Res Commun, 2006, 351: 853-859.

Zhao, B., et al. Exosomal MicroRNAs Derived from Human Amniotic Epithelial Cells Accelerate Wound Healing by Promoting the Proliferation and Migration of Fibroblasts. Stem Cells International, vol. 2018, Article ID 5420463, 10 pages.

Alcaraz A. et al., Autocrine TGF-beta Induces Epithelial to Mesenchymal Transition in Human Amniotic Epithelial Cell, Cell Transplantation, (2013); 22:8, 1351-1367.

European Supplementary Search Report, Europeean Patent No. 20763834.7, dated Nov. 7, 2022.

Turhan-Haktanir N. et al., Evaluation of amniotic fluid as a skin graft storage media compared with RPMI and saline, Burns, (2011); 37:4, 652-655.

Skardal A. et al., Bioprinted Amniotic Fluid-Derived Stem Cells Accelerate Healing of Large Skin Wounds, Stem Cells Translational Medicine, (2012); 1:11, 792-802.

Teodelinda M. et al., Amniotic liquid derived steem cells as reservoir of secreted angiogenic factors capable of stimulating neo-arteriogenesis in an ischemic model, Biomaterials, (2011) 35:15, 3689-3699.

\* cited by examiner

FIG. 3A
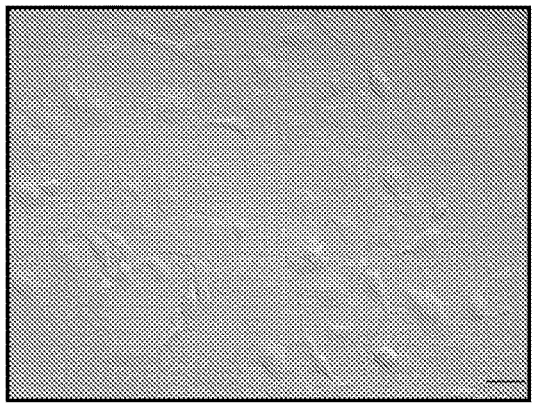
0h DMEM
FIG. 3B
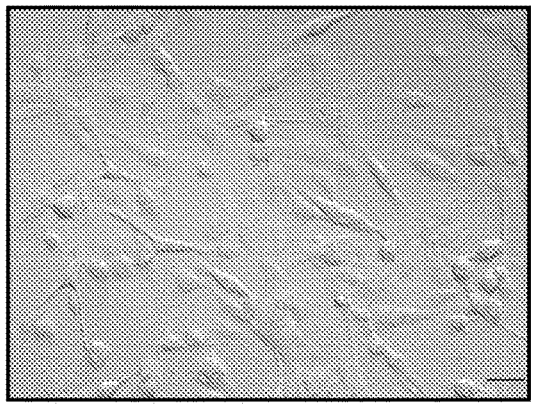
24h DMEM
FIG. 3C
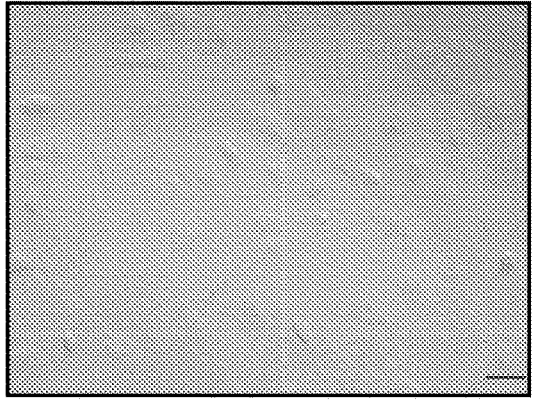
0h SFM2
FIG. 3D
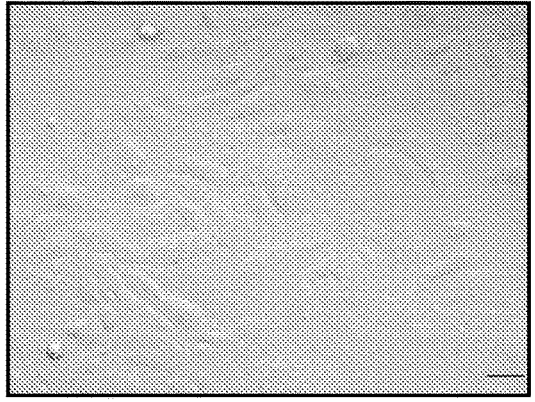
24h SFM2
FIG. 3E
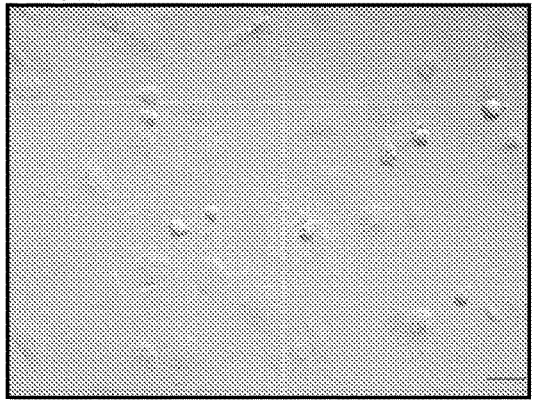
0h SFM1
FIG. 3F
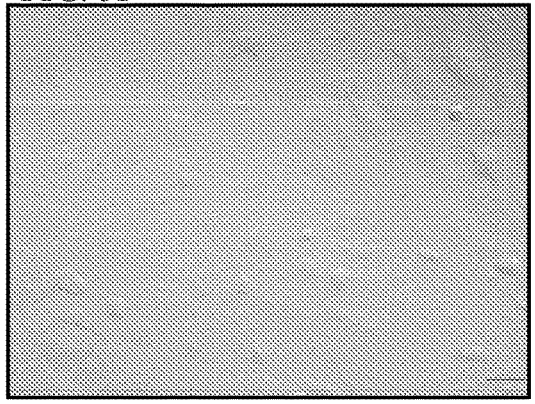
24h SFM1
FIG. 3

| Trypan blue exclusion assay | Bradford assay | sample | Liquid chromatography-mass spectrometry | |
|---|---|---|---|---|
| viable cells (+/- SD) | total protein (microgram/ml) | | proteins identified | % of total |
| N/A | 66 | all proteins | 1043 | 100 |
| 334350 (61384) | 91 | SFM1 | 69 | 6.6 |
| | 79 | co-AC | 824 | 79.0 |
| 43200 (2934) | | AEC | 655 | 62.8 |
| 334000 (12000) | 73 | AFC | 777 | 74.5 |

FIG. 6

| secretome comparison | proteins identified | % of co-AC>0 |
|---|---|---|
| co-AC>0 | 824 | 100 |
| co-AC>BG | 784 | 95.2 |
| co-AC>(BG+AEC) | 452 | 54.9 |
| co-AC>(BG+AFC) | 421 | 51.1 |
| co-AC>(BG+AEC+AFC) | 225 | 27.3 |

FIG. 8

COMPOSITIONS CONTAINING AMNIOTIC COMPONENTS AND METHODS FOR PREPARATION AND USE THEREOF

RELATED APPLICATIONS

This application is a 35 U.S.C. § 371 national stage filing of International Application No. PCT/US2018/047818, filed Aug. 23, 2018, which claims the benefit of U.S. Provisional Patent Application No. 62/549,076, filed Aug. 23, 2017, entitled "COMPOSITIONS CONTAINING AMNIOTIC COMPONENTS AND METHODS FOR PREPARATION AND USE THEREOF", the entire content of both of which is incorporated by reference herein.

TECHNICAL FIELD

The present disclosure relates to compositions containing biologically active components of amniotic fluid and methods of preparation and use thereof.

BACKGROUND

Numerous growth factors are useful in the wound healing and epidermal remodeling processes, and have been successfully applied to treat wounds and for reversing aging and wrinkled skin. Amniotic fluid and tissues contain numerous active biological molecules including proteins, lipids, carbohydrates, and electrolytes; some of which may function as enzymes, hormones, and growth factors. Growth factors are typically proteins that can have diverse biological effects but are characterized as trophic factors that activate pro-growth cell signaling cascades. Several biologically relevant growth factors found in amniotic fluid include epidermal growth factor (EGF), transforming growth factor alpha (TGF-α), transforming growth factor beta (TGF-β), insulin-like growth factors (IGFs), and erythropoietin (EPO). Amniotic fluid also reduces scarring (Ozgenel G Y et al., J Neurosurg 2003; 98: 371-377), in part due to the presence of hyaluronic acid (Gao X et al., Ann Plastic Surg 1994; 33: 128-134).

Thus, amniotic tissue and amniotic fluid are a source of biological components that stimulate tissue repair and promote skin and connective tissue homeostasis. However, there is significant donor-to-donor variation in the molecular composition of amniotic tissue and fluid. In addition, it is unclear whether many important amniotic factors survive the various processes used in the recovery and storage of amniotic fluid. Therefore, the inherent variability in amniotic tissue as well as the different collection and storage conditions is a challenge for standardizing and reproducing the efficacy of these products in a variety of therapeutic applications.

Thus, an important and unmet need remains for consistent amniotic tissue compositions. The presently disclosed subject matter provides such improved compositions, and methods of preparation and use thereof.

SUMMARY

In one embodiment, a method is provided for making a composition having components of amniotic fluid, the method comprising: (a) transferring amniotic epithelial cells (AECs) and amniotic fluid cells (AFCs) to a cell culture system and culturing the AECs and AFCs in a defined medium essentially free of serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; and (d) ensuring the sterility of the conditioned supernatant, wherein the sterile conditioned supernatant is the composition having components of amniotic fluid. The AECs can be attached to a surface of the culture system and the AFCs can be deposited on top of the AECs. The AECs can be mitotically inactivated prior to transferring to the cell culture system. The lipids can comprise arachidonic acid, cholesterol, DL-alpha-tocopherol acetate, linoleic acid, linolenic acid, myristic acid, oleic acid, palmitic acid, palmitoleic acid, and stearic acid.

In one embodiment, a method is provided for making a composition having components of amniotic fluid, the method comprising: (a) transferring at least one of cell types selected from the group consisting of: (i) amniotic fluid cells, (ii) amniotic membrane cells (amniotic epithelial cells or "AEC"), (iii) placental cells, and (iv) umbilical cord cells to a cell culture system and culturing the at least one cell type in a defined medium essentially free of serum to a predetermined target total protein concentration in the culture medium; (b) separating the at least one cell type from the culture medium to obtain a conditioned supernatant; (c) removing large molecules and other cell debris from the conditioned supernatant; and (d) ensuring the sterility of the conditioned supernatant, wherein the sterile conditioned supernatant is the composition having components of amniotic fluid. The defined medium essentially free of serum can consist of a base media, one or more of monothioglycerol, lipids, or polyvinyl alcohol, and optionally one or more antibiotics. The lipids can comprise arachidonic acid, cholesterol, DL-alpha-tocopherol acetate, linoleic acid, linolenic acid, myristic acid, oleic acid, palmitic acid, palmitoleic acid, and stearic acid In one embodiment, a composition is provided having components of amniotic fluid, wherein the composition is produced by a process comprising: (a) transferring amniotic epithelial cells (AECs) and amniotic fluid cells (AFCs) to a cell culture system and culturing the AECs and AFCs in a defined medium essentially free of serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; and (d) ensuring the sterility of the conditioned supernatant, wherein the sterile conditioned supernatant is the composition having components of amniotic fluid.

In one embodiment, a method is provided for preservation of an organ, the method comprising surrounding the organ in a composition having components of amniotic fluid wherein the composition is produced by a process comprising: (a) transferring amniotic epithelial cells (AECs) and amniotic fluid cells (AFCs) to a cell culture system and culturing the AECs and AFCs in a defined medium essentially free of serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; and (e) ensuring sterility of the conditioned supernatant, wherein the sterile conditioned supernatant is the composition having components of amniotic fluid, wherein the organ is preserved in the composition.

In one embodiment, a topical composition is provided for regulating skin condition, the topical composition comprising: i) a safe and effective amount of a composition having components of amniotic fluid; and ii) a carrier, wherein the composition having components of amniotic fluid is produced by a process comprising: (a) transferring amniotic epithelial cells (AECs) and amniotic fluid cells (AFCs) to a cell culture system and culturing the AECs and AFCs in a defined medium essentially free of serum serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; (d) ensuring sterility of the conditioned supernatant; and (e) one or both of concentrating the sterile conditioned supernatant and isolating one or more proteins, microvesicles/exosomes, nucleic acids, or lipids present in the total protein, wherein the one or both of concentrated conditioned supernatant and isolated proteins, microvesicles/exosomes, nucleic acids, or lipids are the composition having components of amniotic fluid.

In one embodiment, a method is provided for regulating a human skin condition which includes applying to human skin at least once a day over at least seven days the topical composition described above.

In one embodiment, a method is provided for tissue repair, the method comprising one of putting on, embedding into, filling, and injecting a tissue with a composition having components of amniotic fluid produced by a process comprising: (a) transferring amniotic epithelial cells (AECs) and amniotic fluid cells (AFCs) to a cell culture system and culturing the AECs and AFCs in a defined medium essentially free of serum serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; and (d) ensuring the sterility conditioned supernatant, wherein the tissue is repaired by the putting on, embedding into, filling, or injecting the tissue with the composition.

BRIEF DESCRIPTION OF THE DRAWINGS

FIG. 3A is an image of AECs plated in DMEM basal media at 0 h according to one or more embodiments of the present disclosure (scale bar denotes 50 µm).

FIG. 3B is an image of AECs plated in DMEM basal media at 24 h according to one or more embodiments of the present disclosure (scale bar denotes 50 µm).

FIG. 3C is an image of AECs plated in SFM2 media at 0 h according to one or more embodiments of the present disclosure (scale bar denotes 50 µm).

FIG. 3D is an image of AECs plated in SFM2 media at 24 h according to one or more embodiments of the present disclosure (scale bar denotes 50 µm).

FIG. 3E is an image of AECs plated in SFM1 media at 0 h according to one or more embodiments of the present disclosure (scale bar denotes 50 µm).

FIG. 3F is an image of AECs plated in SFM1 media at 24 h according to one or more embodiments of the present disclosure (scale bar denotes 50 µm).

FIG. 6 is a table showing analysis by Bradford assay and LC-MS/MS of conditioned SFM1 produced according to the method illustrated in FIG. 4 according to one or more embodiments of the present disclosure. Unconditioned SFM1 (SFM1), the co-AC conditioned SFM1 (co-AC), the AEC conditioned SFM1 (AEC), and the AFC conditioned SFM1 (AFC) were measured for total protein concentration using the Bradford method or the proteome analyzed by liquid chromatography-tandem mass spectrometry (LC-MS/MS) to determine unique proteins present in each sample and the percent of proteins per sample relative to all proteins identified in each of the 4 groups assayed.

FIG. 8 is a table showing the quantitative amounts of the numbers and percentages of proteins identified by LC-MS/

Figure 4:
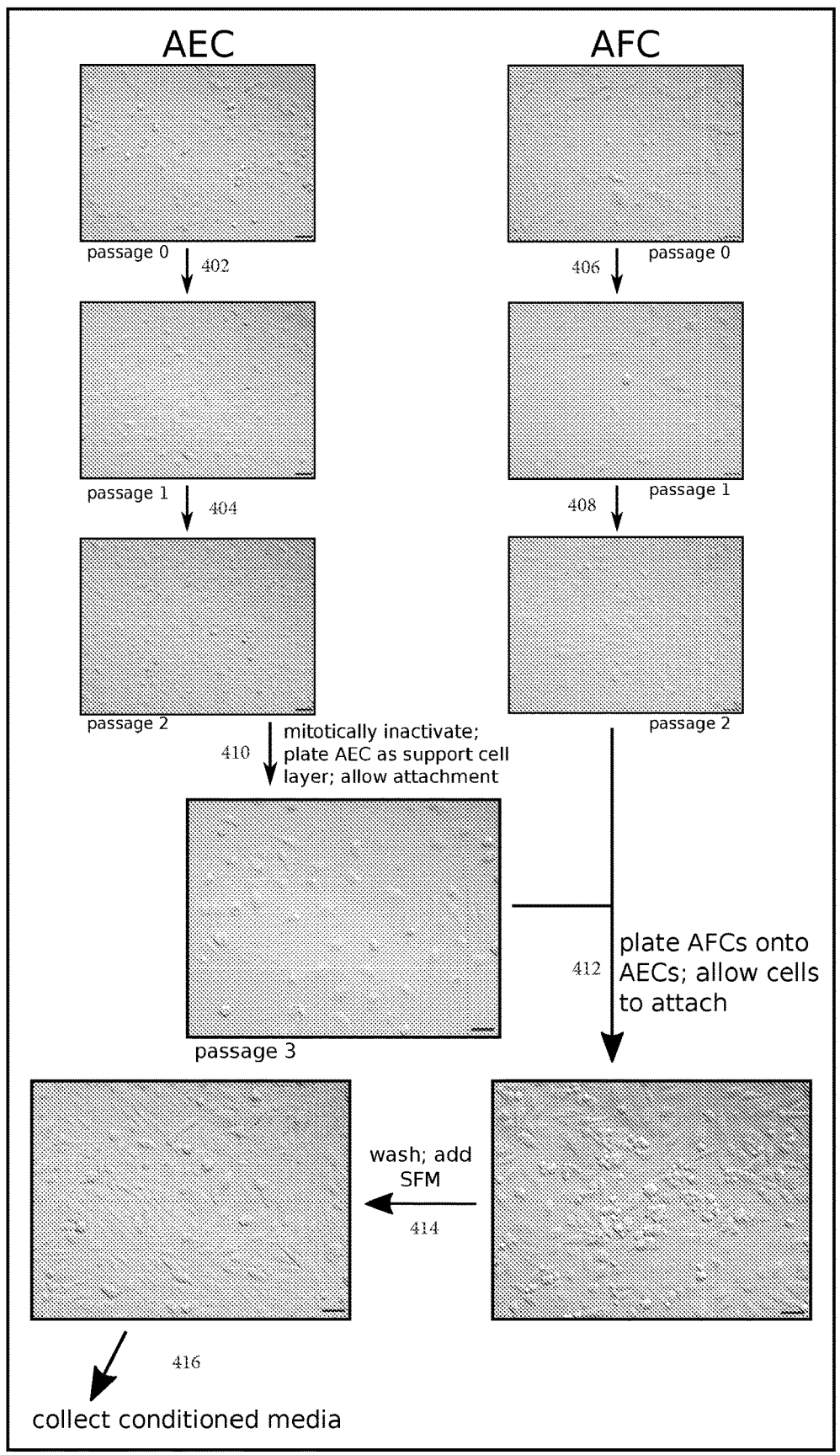
FIG. 4 is a flow diagram showing methods for making compositions having components of amniotic fluid according to one or more embodiments of the present disclosure (scale bar denotes 50 µm in each image).

MS in the conditioned SFM1 from the co-culture of the AECs and AFCs according to the method illustrated in FIG. 4 according to one or more embodiments of the present disclosure. The first row is proteins quantities measured by normalized total spectral counts for the co-culture of the AECs and AFCs in SFM1 that are greater than zero (co-AC>0); the second row is proteins detected in co-AC after subtracting the background proteins present in unconditioned SFM1 (co-AC>BG), the third row is proteins whose level measured in co-AC is higher than background proteins plus proteins identified in AEC alone-conditioned SFM1 (co-AC>(BG+AEC)), the fourth row is proteins whose level measured in co-AC is higher than background proteins plus proteins identified in AFC alone-conditioned SFM1 (co-AC>(BG+AFC)), and the fifth row is proteins whose level measured in co-AC is higher than background proteins plus proteins identified in AEC alone-conditioned SFM1 plus proteins identified in AFC alone-conditioned SFM1 (co-AC>(BG+AEC+AFC)). For all protein level analyses above, normalized spectral count values of co-AC were used to subtract normalized spectral count values from the other comparative groups (AEC only, AFC only, and AEC plus AFC).

Figure 9:
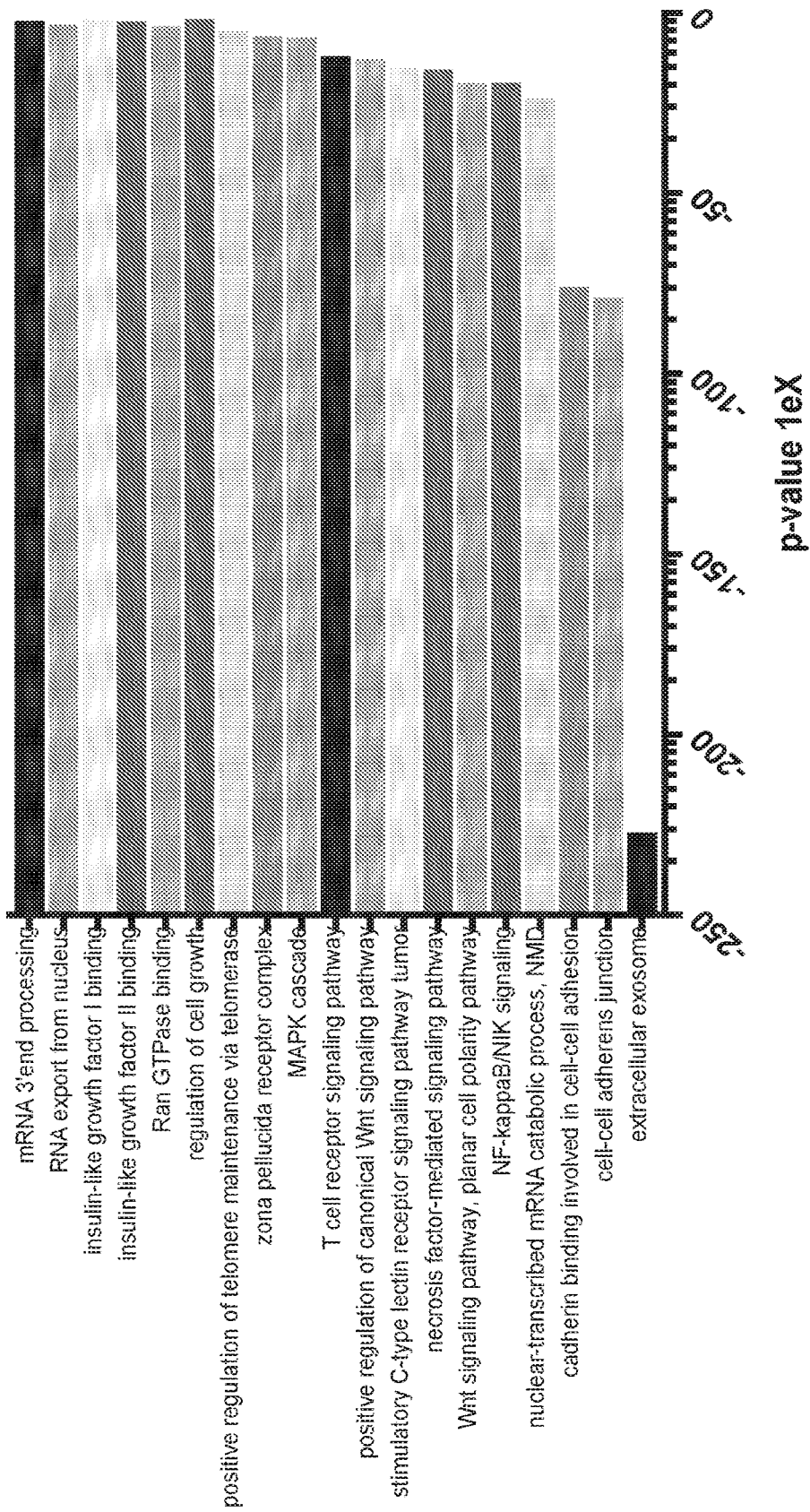

FIG. 9 is a bar graph showing the gene ontology (GO) term analysis identifying significantly enriched biological pathways from protein groups identified in the conditioned SFM1 from the co-culture of the AECs and AFCs according to the method illustrated in FIG. 4 according to one or more embodiments of the present disclosure. LC-MS/MS data from the conditioned SFM1 was compared to unconditioned SFM1 LC-MS/MS data (input as background data set) to derive significantly enriched ($p \leq 0.05$) GO terms. Selected GO terms are shown on the Y-axis and p-values are plotted on the X-axis as 1eX with X being the value shown on the X-axis.

DETAILED DESCRIPTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates. Following long-standing patent law convention, the terms "a," "an," and "the" refer to "one or more" when used in this application, including the claims. Thus, for example, reference to "a defined medium" includes a plurality of defined media, unless the context clearly is to the contrary, and so forth.

Throughout this specification and the claims, the terms "comprise," "comprises," and "comprising" are used in a non-exclusive sense, except where the context requires otherwise. Likewise, the terms "having" and "including" and their grammatical variants are intended to be non-limiting, such that recitation of items in a list is not to the exclusion of other like items that can be substituted or added to the listed items.

Throughout this specification and the claims, the phrase "amniotic membrane (AM) cells" is used interchangeably with the phrase "amniotic epithelial cells (AEC)" and is intended to include all cell types derived from amniotic membrane of which the vast majority consists of amniotic epithelial cells.

Throughout this specification and the claims, the term "base media" is intended to mean a media that does not contain added serum (i.e., is essentially free of serum). Examples of base media include, but are not limited to, DMEM/F12, DMEM, F12, and IMDM.

The presently disclosed subject matter provides compositions that contain active biological components of amniotic fluid including growth factors and other proteins, carbohydrates, lipids and metabolites. The compositions of the present disclosure having components of amniotic fluid can be useful for a range of therapeutic treatments including, for example, tissue repair such as wound healing, promotion of cell/tissue homeostasis, and regulation of skin condition. In addition, the compositions of the present disclosure are provided for use in organ preservation, such as for use in organ transplant procedures. In contrast to prior art amniotic fluid compositions, the compositions of the present disclosure can be reproducibly produced, without the inherent variability of amniotic fluid from separate donors. Another advantage of the compositions of the present disclosure is that they are free of fetal waste products including but not limited to the high concentration of urea observed in amniotic fluid.

Compositions are provided that contain biologically active components of amniotic fluid. For the purpose of this specification and claims, the phrase "biologically active components of amniotic fluid" is used interchangeably with "biologically active components" and "components" and is intended to include all types of molecules secreted from cells of amniotic tissue including, but not limited to, proteins, enzymes, hormones, growth factors, cytokines, lipids, carbohydrates, electrolytes, and extracellular vesicles containing cargo such as the foregoing listed molecules. The terms "extracellular vesicles", "microvesicles", "exosomes", "secreted microvesicles", and "secreted vesicles" are used interchangeably herein for the purposes of the specification and claims.

Figure 1:
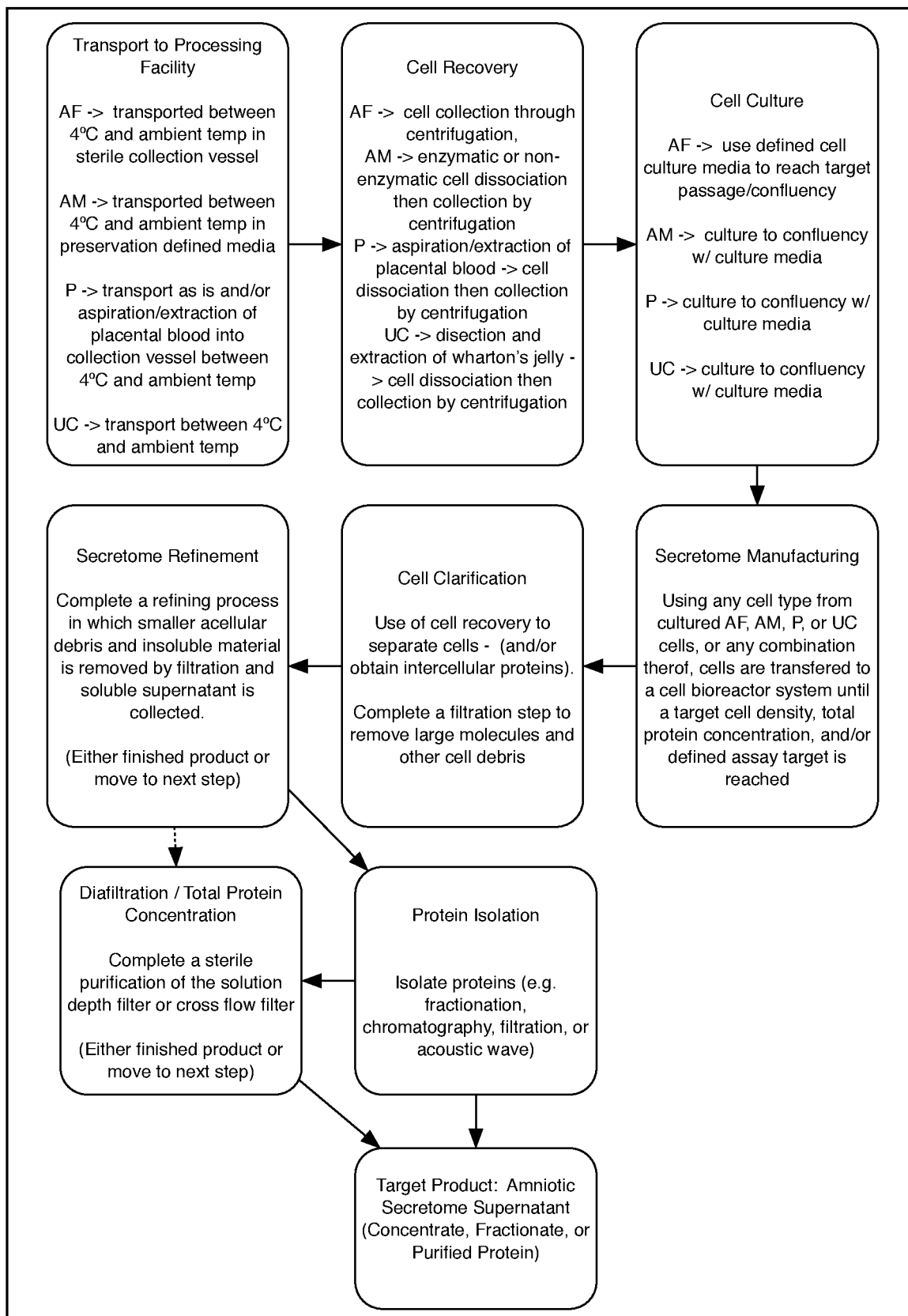
FIG. 1 is a flow diagram showing methods for making compositions having components of amniotic fluid according to one or more embodiments of the present disclosure.

In one embodiment, the compositions are produced from cells derived from a donor of amniotic tissue according to a method illustrated in the flow chart of FIG. 1. Amniotic tissues including one or a combination of amniotic fluid (AF), amniotic membrane (AM), placenta (P), and umbilical cord (UC) can be obtained from a donor and processed according to standard procedures as outlined in FIG. 1. The donor can be a mammal and the cells can be processed without having been previously frozen. The mammal can be a human. The donor can be a C-section donor. Cells can be recovered from the one or a combination of tissues using standard procedures such as those outlined in FIG. 1.

One or more types of cells including, but not limited to, AF cells, AEC cells, P cells, and UC cells can be recovered from the amniotic tissue using standard procedures as outlined in FIG. 1. These cells may then be cultured to expand the cells. Whether or not the cells are expanded first, the cells may be frozen for storage and later use. In one embodiment, the cells are transformed and converted to a cell line for use in the methods of the present disclosure.

The one or more types of recovered cells (AF cells, AEC cells, P cells, and UC cells) can be expanded or cultured to a target passage as outlined in FIG. 1. The culturing can be in acellular cytokine-rich amniotic fluid (AFCK), in media enhanced with AFCK, or in another defined cell culture media using standard cell culture procedures. In one embodiment, the one or more types of recovered cells are cultured separately.

The one or more types of recovered cells (AF cells, AEC cells, P cells, and UC cells) are transferred to a cell culture system and cultured in a defined medium essentially free of serum until a point where a predetermined total protein concentration is present in the conditioned cell medium. The defined medium essentially free of serum can consist of a base media, one or more of monothioglycerol, lipids, or polyvinyl alcohol, and optionally one or more antibiotics. In one embodiment, the AECs can be mitotically inactivated prior to transferring to the cell culture system.

In the methods of the present disclosure, the cell culture system can be tissue culture flasks/plates, a bioreactor, a suspension bioreactor, or an adherent bioreactor. Growth factors and other active biological components of the amniotic tissue-derived cells are secreted by the cultured living cells. At the predetermined point, the liquid medium portion of the culture system contains conditioned cell supernatant that is rich in secreted factors. The growth factors and other extracellular components including proteins and extracellular vesicles containing cargo are secreted into the nutrient medium in which they are cultured. In the methods for making the compositions of the present disclosure, the at least one cell type can be separated from the defined medium essentially free of serum once the cells reach the predetermined target total protein concentration to obtain a conditioned supernatant.

The conditioned supernatant can be filtered to remove large molecules and other cell debris. The sterility of the conditioned supernatant is ensured, and in some cases one or more procedures are performed to sterilize the conditioned supernatant. The sterilization procedure can be one or more filtration procedures. In this manner, the sterile conditioned supernatant yields a composition having biologically active components of amniotic fluid. An advantage of the compositions of the present disclosure, in contrast to amniotic fluid derived from a single donor, is that the compositions can be reproducibly produced to avoid large deviations in the amounts of biologically active components and can be produced free of fetal waste products including but not limited to the high concentration of urea observed in amniotic fluid.

Thus, in one embodiment, a method is provided for making a composition having components of amniotic fluid, the method including: (a) transferring at least one of cell types selected from the group consisting of: (i) amniotic fluid cells, (ii) amniotic membrane cells, (iii) placental cells, and (iv) umbilical cord cells to a cell culture system and culturing the at least one cell type in a defined medium essentially free of serum; (b) separating the at least one cell type from the culture medium to obtain a conditioned supernatant; (c) removing large molecules and other cell debris from the conditioned supernatant; and (d) ensuring the stability of the conditioned supernatant, wherein the sterile conditioned supernatant is the composition having components of amniotic fluid. The defined medium essentially free of serum can consist of a base media, one or more of monothioglycerol, lipids, or polyvinyl alcohol, and optionally one or more antibiotics.

In the compositions and methods of the present disclosure, the cell types used in the process for producing the composition having the components of amniotic fluid can consist of at least two of the cell types (i)-(iv). The cell types can consist of at least three of the cell types (i)-(iv). The cell types can consist of the four cell types (i)-(iv).

FIGS. 2A-2D are images of AECs and AFCs recovered and cultured as illustrated in FIG. 1 and stained with the stem cell marker stage-specific antigen 4 (SSEA4) and DAPI (stains all DNA/nuclei). Specifically, FIG. 2A shows AECs stained with antibody recognizing SSEA4, FIG. 2B shows AECs stained with DAPI, FIG. 2C shows AFCs stained with antibody recognizing SSEA4, and FIG. 2D shows AFCs stained with DAPI. The results show that the majority of propagated cells are amniotic stem cells rather than amniotic fibroblast, myoblast, or other non-stem cell types.

FIGS. 3A-3F are images of AECs comparing incubation in 3 different types of serum free media for 24 hours. Specifically, FIGS. 3A and 3B show the results with DMEM, FIGS. 3C and 3D show the results with SFM2, and FIGS. 3E and 3F show the results with SFM1. The cells in FIG. 3B appear relatively more spindly, having taken on more of a fibroblast-like morphology, in the DMEM media, whereas the cells incubated for 24 h in both SFM1 and SFM2 maintained their epithelial morphology. The SFM2 consists of DMEM/F12 and 1% penicillin/streptomycin. The SFM1 consists of 50% IMDM, 50% F12, 1 mg/ml polyvinyl alcohol, 1% chemically-defined lipid concentrate, 450 µM monothioglycerol, and 1% penicillin/streptomycin.

In one embodiment, a method for making a composition having components of amniotic fluid is provided and is illustrated in FIG. 4. The method comprises transferring AECs and AFCs to a cell culture system and culturing the AECs and AFCs in a defined medium essentially free of serum, separating the AECs and AFCs from the culture medium to obtain a conditioned supernatant, removing large molecules and other cell debris from the conditioned supernatant, and ensuring the sterility of the conditioned supernatant, wherein the conditioned supernatant is the composition having components of amniotic fluid. As is illustrated in steps 402, 404, 406, and 408 of FIG. 4, each of the AECs and AFCs can be expanded in culture prior to transferring the cells to the cell culture system by passaging the cells one, two, three or more times. In one embodiment, the AECs can be attached to a surface of the culture system and the AFCs can be deposited on top of the AECs, as is illustrated in steps 410 and 412 of FIG. 4. The AECs can be mitotically inactivated prior to transferring to the cell culture system as illustrated in step 410 of FIG. 4. Step 414 of FIG. 4 illustrates culturing the AECs and AFCs in a defined medium essentially free of serum. In one embodiment, the AECs and AFCs are cultured in a suspension culture rather than by attachment to a surface as shown in FIG. 4. The AECs and AFCs can be cultured until a predetermined target total protein concentration in the conditioned supernatant. The step of separating the AECs and AFCs from the culture medium to obtain a conditioned supernatant is illustrated by step 416 of FIG. 4. The terms "conditioned supernatant" and "amniotic cell conditioned media (ACCM)" are herein used interchangeably and refer to the composition having components of amniotic fluid.

Figure 5:
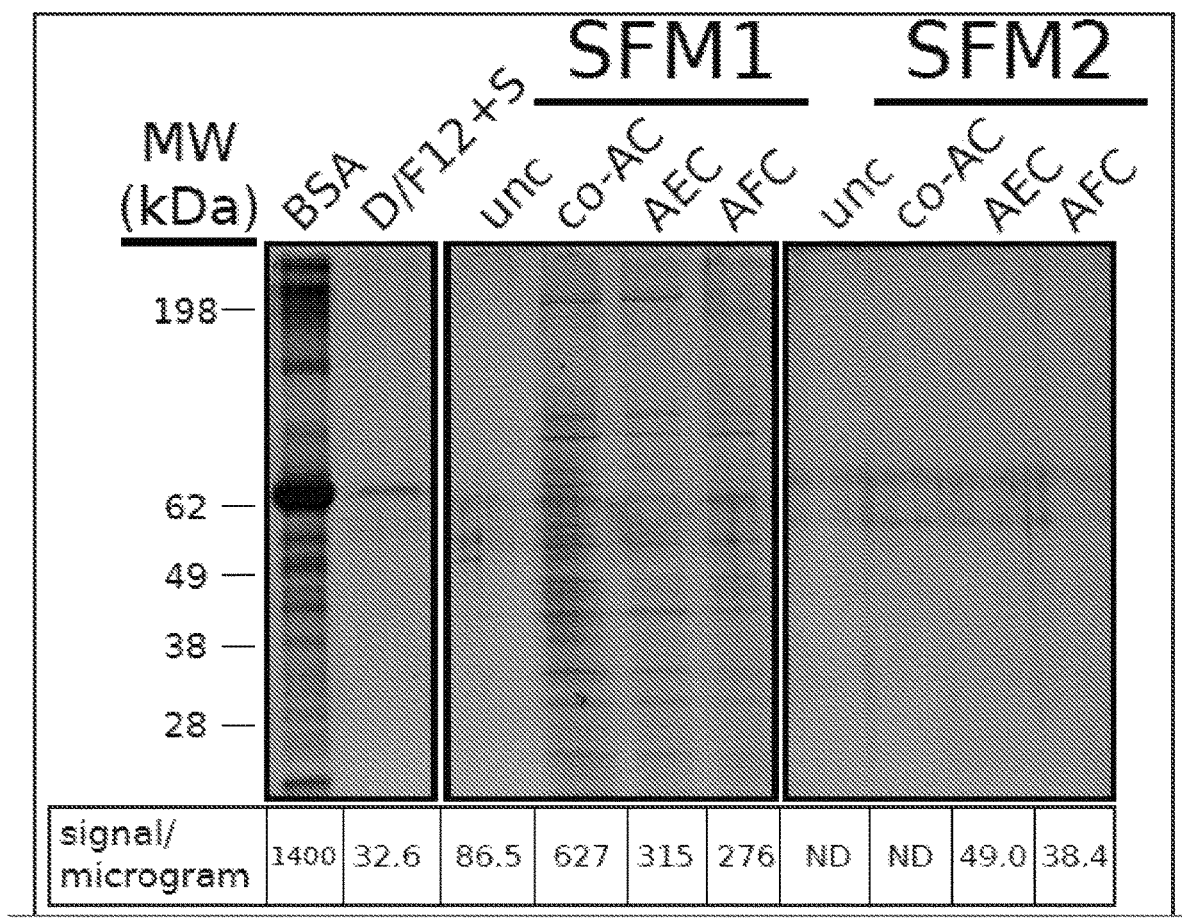
FIG. 5 is a an image of an SDS PAGE gel showing that co-culture of AECs and AFCs (co-AC) in a defined media, SFM1, according to the method illustrated in FIG. 4 results in increased total protein secretion and increased protein complexity according to one or more embodiments of the present disclosure. In contrast, co-culture in a different defined media, SFM2, resulted in no apparent increase in protein secretion as compared to unconditioned media. One microgram total protein was loaded in lanes (from left to right) consisting of bovine serum albumin (BSA), DMEM/F12+10% fetal bovine serum (D/F12+S), unconditioned serum-free media 1 (SFM1; unc), co-AC conditioned SFM1 (SFM1; co-AC), AEC conditioned SFM1 (SFM1; AEC), AFC conditioned SFM1 (SFM1; AFC), unconditioned serum-free media 2 (SFM2; unc), co-AC conditioned SFM2 (SFM2; co-AC), AEC conditioned SFM2 (SFM2; AEC), and AFC conditioned SFM2 (SFM2; AFC), and electrophoresed on 10% SDS-polyacrylamide gel then silver stained. The signal intensity calculated per lane is shown as "signal/microgram" at the bottom of the gel. The gels were scanned on a Li-Cor Odyssey CLx and signal per microgram protein determined by generating a region of interest consisting of each lane and determining signal counts using ImageStudio software program. Molecular weight in kilodaltons (kDa) is shown on the left; ND denotes no signal detected above background; all conditioned medias analyzed were generated by 24 h culture and unconditioned medias by 24 h incubation in a well of the same culture plate but minus cells.

FIG. 5 shows analysis by SDS-PAGE and silver staining of the amniotic cell conditioned media produced using two different types of serum free media (SFM1 and SFM2) at step 414 in the method. As can be seen in FIG. 5, the co-culture of the AECs and AFCs (co-AC) in the defined media, SFM1, resulted in increased total protein secretion and increased protein complexity (i.e., the same amount of total protein (1 µg) is added in each lane, but the co-AC conditioned media shows both different bands present and an increased signal intensity relative to AECs or AFCs alone). Surprisingly, the co-culture of the AECs and AFCs in the SFM2 media shows no apparent protein secretion at all compared to unconditioned media. These data illustrate a synergistic effect of the co-culture of the AECs and AFCs in the SFM1 media that can yield a conditioned media having both increased protein concentration and increased protein complexity.

FIG. 6 shows analysis by Bradford assay and LC-MS/MS of the amniotic cell conditioned medium (ACCM) from the co-culture of the AECs and AFCs in the SFM1. As can be seen in FIG. 6, the co-culture of the AECs and AFCs in the SFM1 media according to the method described above resulted in the highest total protein concentration by Bradford assay. Using the LC-MS/MS method a higher number of proteins (by identity) is observed in ACCM compared to AECs or AFCs alone. The viable cell results from the trypan blue exclusion assay show that the AFC alone cell count is the same as the co-AC cell count, indicating that the higher protein concentration and increased number of distinct protein identities results from the same number of cells per well. These data show the synergistic effect of the co-culture of the AECs and AFCs in the SFM1 media that can yield a conditioned media having both increased protein concentration and complexity.

Figure 7:
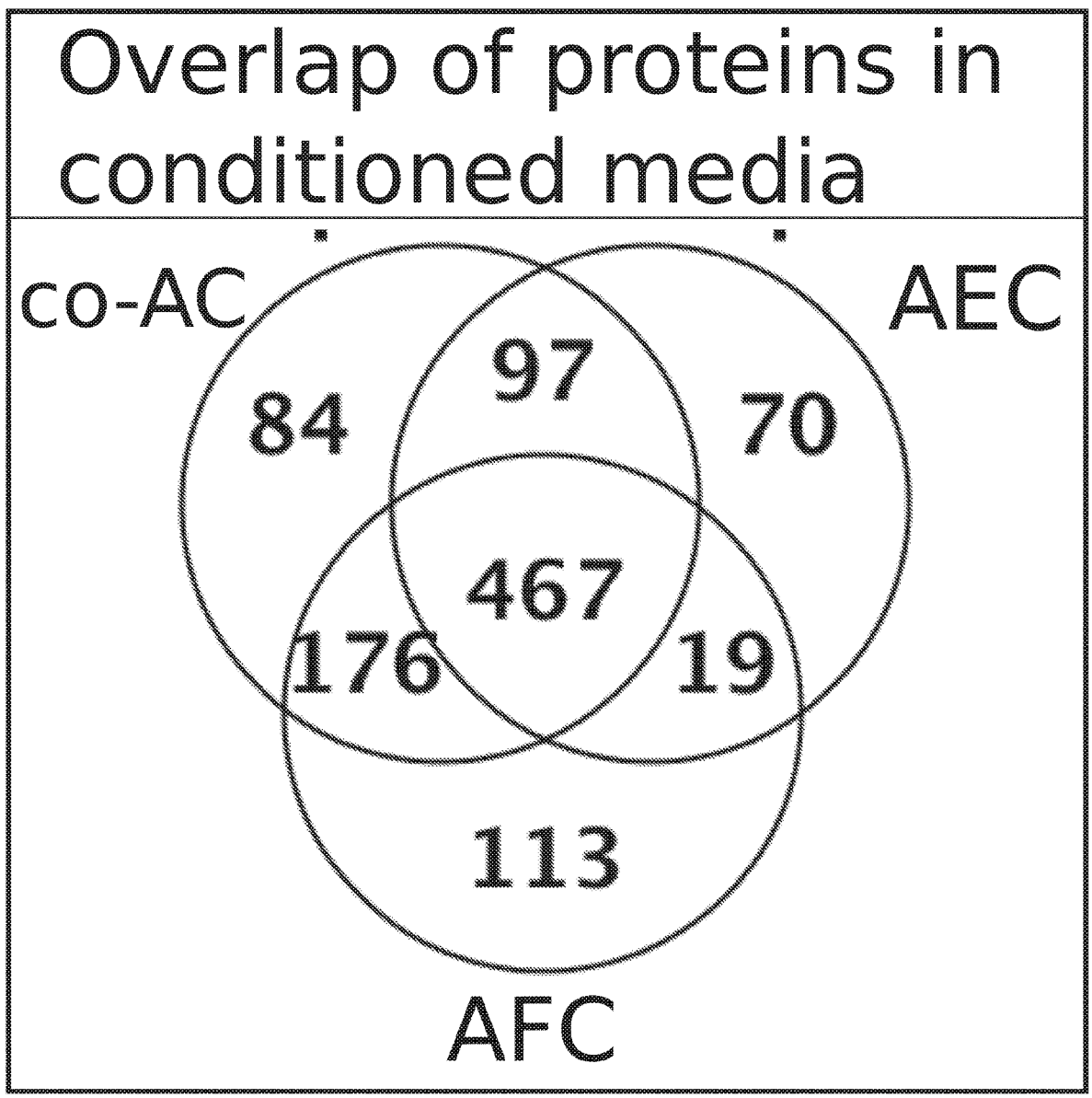
FIG. 7 is a Venn diagram of the LC-MS/MS data reported in FIG. 6 showing the overlap or distinct proteins (by identity) secreted into SFM1 using AFCs, AECs, or co-ACs cultured. The analysis indicates that the co-culture of the AECs and AFCs in the SFM1 media yields 84 unique proteins not identified in either the AEC- or AFC-alone conditioned SFM1 according to one or more embodiments of the present disclosure.

FIG. 7 is a Venn diagram of the LC-MS/MS data shown in FIG. 6 showing that the co-culture of the AECs and AFCs in the SFM1 media yields 84 unique proteins by identity not observed in either the AEC- or AFC alone conditioned SFM1. This result illustrates the synergistic effect of the co-culture of the AECs and AFCs in the SFM1 media that can yield a conditioned media with increased protein complexity.

FIG. 8 shows, by quantitative analysis, the number and percentage of proteins identified by LC-MS/MS in the conditioned SFM1 from the co-culture of the AECs and AFCs. The data in FIG. 8 show that the co-culture of the AECs and AFCs yielded quantitatively higher levels of proteins than in either AECs only, AFCs only, or the sum of AECs and AFCs only. The results in FIG. 8 show that the quantity of 225 of the identified proteins (27.3% of the total) are present at a higher level in the conditioned media from co-culture of AECs and AFCs than the additive level of AEC alone-conditioned SFM1 plus AFC alone-conditioned SFM1. These data illustrate, using a quantitative analysis of the proteome, the synergistic effect of the co-culture of the AECs and AFCs in the SFM1 media that can yield a conditioned media with increased protein concentration and complexity, and rule-out a simply additive effect of AFC and AEC conditioning alone.

FIG. 9 shows the results of Gene ontology (GO) term analysis identifying significantly enriched biological pathways represented within the proteome of conditioned SFM1 from the co-culture of the AECs and AFCs according to the methods of the present disclosure. LC-MS/MS data from the conditioned SFM1 was compared to unconditioned SFM1 LC-MS/MS data to derive enriched ($p \leq 0.05$) GO terms. The GO result showing enrichment of various types of RNA metabolism indicates that the amniotic cell conditioned media of the present disclosure can promote overall cell homeostasis by promoting proper RNA stability, localization, translation, and decay. The identification of proteins enriched in NF-kappa B/NIK signaling pathway, T cell receptor signaling pathway, tumor necrosis factor-mediated signaling pathway, and MAPK cascade indicates that ACCM can function as an anti-inflammatory and protect against cell death in a variety of pathological conditions. The identification of proteins significantly enriched in Wnt signaling pathway, planar cell polarity pathway, positive regulation of canonical Wnt signaling pathway, and positive regulation of telomere maintenance via telomerase indicates that ACCM can function to regulate stem cell self-renewal/differentiation to specific target cell types. The identification of proteins enriched in MAPK cascade, positive regulation of telomere maintenance via telomerase, regulation of cell growth, insulin-like growth factor I and II binding indicate that ACCM can function to promote cell growth/homeostasis and/or support metabolic activity. The identification of proteins enriched in cell-cell adherens junction and cadherin binding involved in cell-cell adhesion indicate ACCM can promote cell attachment to a substrate. The identification of proteins enriched in extracellular exosomes indicates ACCM can mediate vesicular transport of cargo (proteins, nucleic acid, lipids and other biomolecules) to cells/tissues. Additionally, these findings indicate that ACCM is enriched in the types of proteins present in amniotic fluid.

In the methods for making a composition having components of amniotic fluid of the present disclosure, the defined medium essentially free of serum can consist of a base media one or more of monothioglycerol, lipids, or polyvinyl alcohol and, optionally, one or more antibiotics. The lipids can comprise arachidonic acid, cholesterol, DL-alpha-tocopherol acetate, linoleic acid, linolenic acid, myristic acid, oleic acid, palmitic acid, palmitoleic acid, and stearic acid.

The methods of the present disclosure can further include concentrating the sterile conditioned supernatant.

The methods of the present disclosure can further include isolating one or more of the proteins, microvesicles/exosomes, nucleic acids, or lipids present in the sterile conditioned supernatant. The isolation of one or more of the proteins, microvesicles/exosomes, nucleic acids, or lipids can be through fractionation, filtration, chromatography or combinations thereof.

The cell types of the present disclosure can be derived from mammalian tissue without having been previously frozen. The mammalian tissue can be a human tissue.

In one embodiment, a method is provided for preservation of an organ, the method including surrounding the organ in a composition having components of amniotic fluid produced according to any of the methods described herein, wherein the organ is preserved in the composition. In one embodiment, a method is provided for preservation of an organ, the method including perfusing the organ in a composition having components of amniotic fluid produced according to any of the methods described herein. A perfusion device can be used for the perfusing. The organ can be for use as an organ in a transplant procedure.

In one embodiment, the process for producing a composition having components of amniotic fluid comprises: (a) transferring at least one of cell types selected from the group consisting of: (i) amniotic fluid cells, (ii) amniotic membrane cells, (iii) placental cells, and (iv) umbilical cord cells to a cell culture system and culturing the at least one cell type in a defined medium essentially free of serum to a predetermined target total protein concentration in the culture medium; (b) separating the at least one cell type from the culture medium to obtain a conditioned supernatant; (c) removing large molecules and other cell debris from the conditioned supernatant; (d) ensuring the sterility of the conditioned supernatant; and (e) one or both of concentrating the sterile conditioned supernatant and isolating one or more proteins, microvesicles/exosomes, nucleic acids, or lipids present in the total protein, wherein the one or both of concentrated conditioned supernatant and isolated proteins, microvesicles/exosomes, nucleic acids, or lipids are the composition having components of amniotic fluid. The defined medium essentially free of serum can consist of a base media, one or more of monothioglycerol, lipids, or polyvinyl alcohol, and optionally one or more antibiotics.

In another embodiment, the process for producing a composition having components of amniotic fluid comprises: (a) transferring amniotic epithelial cells (AECs) and amniotic fluid cells (AFCs) to a cell culture system and culturing the AECs and AFCs in a defined medium essentially free of serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; and (d) ensuring the sterility of the conditioned supernatant, wherein the sterile conditioned supernatant is the composition having components of amniotic fluid.

In one embodiment, a topical composition is provided for regulating skin condition, the topical composition including: i) a safe and effective amount of a composition having components of amniotic fluid; and ii) one or more carriers. The one or more carriers can can consist of one or more active or inactive agents. The active or inactive agents can include, but are not limited to, moisturizing agents, vitamins, and anti-oxidants. The composition having components of amniotic fluid is produced by a process as described herein.

The topical composition can include from about 0.1 to about 20% of a moisturizing agent. The moisturizing agent can include, but is not limited to, one or more of panthenol, pantothenic acid derivatives, glycerin, glycerol, dimethicone, petrolatum, hyaluronic acid, or ceremides, and mixtures thereof.

The topical composition can include a vitamin $B_3$ compound. The vitamin B3 compound can be tocopherol nicotinate.

The topical composition can include an anti-oxidant. The anti-oxidant can be one or a combination of tocopherol or esters of tocopherol.

The topical composition can be in the form of a liquid, lotion, cream, gel, foam, mousse, spray, paste, powder, or solid.

In one embodiment, a method is provided for regulating a human skin condition which includes applying to human skin at least once a day over at least seven days the topical composition described above. The method can include applying the topical composition to human skin at least twice a day over at least fourteen days.

Regulating skin condition includes one or more of inducing increased skin integrity by cell renewal; enhancing water content or moisture of skin; reducing trans epidermal water loss, skin flaking, and scaling; improving skin thickness; enhancing skin tensile properties; reducing the appearance of dermal fine lines and wrinkles; improving skin texture; reducing skin pores size; enhancing skin smoothness; improving skin age spots; improving skin tone; or improving the appearance of scars and skin abrasions.

In one embodiment, a method is provided for tissue repair, the method including one of putting on, embedding into, filling, and injecting a tissue with a composition having components of amniotic fluid produced by a process described herein. In one embodiment, the process for producing a composition having components of amniotic fluid comprises: (a) transferring at least one of cell types selected from the group consisting of: (i) amniotic fluid cells, (ii) amniotic membrane cells, (iii) placenta cells, and (iv) umbilical cord cells to a cell culture system and culturing the at least one cell type in a defined medium essentially free of serum to a predetermined target total protein concentration in the culture medium; (b) separating the at least one cell type from the culture medium to obtain a conditioned supernatant; (c) removing large molecules and other cell debris from the conditioned supernatant; and (d) ensuring the sterility of the conditioned supernatant. The defined medium essentially free of serum can consist of a base media, one or more of monothioglycerol, lipids, or polyvinyl alcohol, and optionally one or more antibiotics.

In another embodiment, the process for producing a composition having components of amniotic fluid, comprises: (a) transferring amniotic epithelial cells (AECs) and amniotic fluid cells (AFCs) to a cell culture system and culturing the AECs and AFCs in a defined medium essentially free of serum consisting of a base media; one or more of monothioglycerol, lipids, or polyvinyl alcohol; and, optionally, one or more antibiotics; (b) separating the AECs and AFCs from the culture medium to obtain a conditioned supernatant; (c) removing large molecules and other cell debris from the conditioned supernatant; and (d) ensuring the sterility of the conditioned supernatant, wherein the sterile conditioned supernatant is the composition having components of amniotic fluid.

The tissue can be repaired by the putting on, embedding into, filling, or injecting of the tissue with the composition having the active components of amniotic fluid, without the significant variability associated with amniotic fluid derived from a single donor.

The tissue repair can include, but is not limited to, repair of dermal, scar, cartilage, tendon, ligament, muscle, bone, periodontal, cardiovascular, hematologic, pulmonary, urologic, ophthalmic, liver, or kidney tissue, or combinations thereof.

The tissue repair can include, but is not limited to, promotion of cell/tissue homeostasis, reducing inflammation, repair of wounds and burns, infection treatment, sepsis treatment, repair of scarring, preventing post-operative scarring, joint repair, rheumatoid arthritis treatment, psoriatic arthritis treatment, gout treatment, bursitis treatment, joint replacement surgery, tendon repair, tendinitis treatment, rotator cuff repair, muscle repair, repair, osteoarthritis treatment, arthritis treatment, male urologic dysfunction treatment, Critical Limb Ischemia treatment, Intermittent Claudication treatment, Buerger's Disease treatment, Ischemic Heart Disease treatment, Diastolic Heart Failure treatment, bronchopulmonary dysplasia, chronic obstructive pulmonary disease, ophthalmic disorders, and reversal of aging. In one embodiment, the composition produced according to the process described herein containing active components of amniotic fluid is a dermal, cartilage, or bone gel.

EXAMPLES

Example 1

Optimization of Media for Cell Growth

The AECs were obtained from fresh Caesarean birth placental tissue by removing the amnion, thoroughly and repeatedly washing the tissue with phosphate-buffered saline (PBS), detaching (with 0.25% trypsin/1 mM EDTA) through 3 incubations and wash-outs, and collecting the AECs by centrifugation, or purchased from commercial vendor. The AECs were either immediately plated onto collagen-coated tissue culture dishes/flasks in propagation media (see below) or cryopreserved in knockout serum replacement containing 10% DMSO for later expansion. The AFCs were freshly obtained from full-term elective Caesarean birth donor amniotic fluid. The amniotic fluid was immediately processed by first passing through 100 μm cell strainer to remove vernix/larger debris then collected by centrifugation. The resulting cell pellet was resuspended and plated for an initial expansion in AFC propagation media (see below), then subsequently expanded or cryopreserved in propagation media containing 10% DMSO for later expansion. All cell culture expansion and experiments were performed in standard 37 C, 5% CO2 tissue culture incubator.

Figure 2:
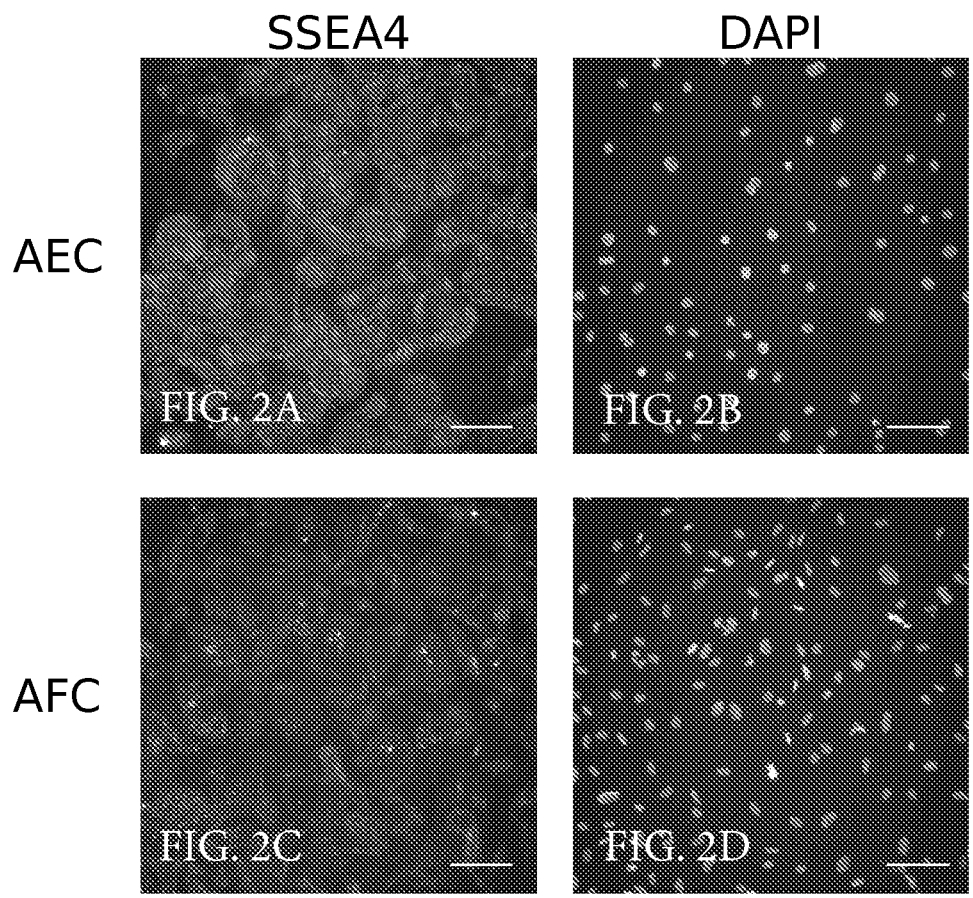
FIG. 2A is an image of amniotic epithelial cells (AECs) stained with an antibody recognizing SSEA4 according to one or more embodiments of the present disclosure (scale bar denotes 100 µm).
FIG. 2B is an image of AECs stained with DAPI according to one or more embodiments of the present disclosure (scale bar denotes 100 µm).
FIG. 2C is an image of amniotic fluid cells (AFCs) stained with an antibody recognizing SSEA4 according to one or more embodiments of the present disclosure (scale bar denotes 100 µm).
FIG. 2D is an image of AFCs stained with DAPI according to one or more embodiments of the present disclosure (scale bar denotes 100 µm).

Both the AECs and AFCs were propagated in media (AEC Propagation media: DMEM/F12, 10% FBS, 1.05 mM $Ca^{2+}$, 10 ng/ml EGF, 1% penicillin/streptomycin and AFC propagation media: DMEM, 10% FBS, 30% amniotic fluid, 1% penicillin/streptomycin) and stained with the stem cell marker stage-specific antigen 4 (SSEA4) and DAPI (stains all DNA/nuclei). The images are shown in FIG. 2. Specifically, panel 2A shows AECs stained with antibody recognizing SSEA4, panel 2B shows AECs stained with DAPI, panel 2C shows AFCs stained with antibody recognizing SSEA4, and panel 2D shows AFCs stained with DAPI. The results show that the majority of propagated cells are amniotic stem cells rather than amniotic fibroblast, myoblast, or other non-stem cell types.

An experiment was performed in which maintenance of AECs' epithelial morphology was tested in three types of serum free media, as a read-out for cell homeostasis. For the experiment to test serum-free media types' effect on cell morphology, mitotically inactivated AECs were plated on collagen-coated tissue culture treated plates and allowed to attach overnight in propagation media; the following day propagation media was removed, cells were washed 3× in PBS then serum-free medias were added to each well containing AECs. The 3 different types of serum free media that were tested are listed below:

DMEM
Dulbecco's Modified Eagle's Media (DMEM; Thermo/Fisher Scientific, Waltham, Mass., USA)
1% penicillin/streptomycin (Thermo/Fisher Scientific, Waltham, Mass., USA)
SFM2:
Dulbecco's Modified Eagle's Media/F12 (DMEM/F12; Thermo/Fisher Scientific, Waltham, Mass., USA)
1% penicillin/streptomycin (Thermo/Fisher Scientific, Waltham, Mass., USA)
SFM1:
50% Iscove's Modified Dulbecco's Media (IMDM; Thermo/Fisher Scientific, Waltham, Mass., USA)
50% F12 (Thermo/Fisher Scientific, Waltham, Mass., USA)
1 mg/ml polyvinyl alcohol (Sigma-Aldrich, St. Louis, Mo., USA)
1% chemically-defined lipid concentrate (Thermo/Fisher Scientific, Waltham, Mass., USA)
450 uM monothioglycerol (Sigma-Aldrich, St. Louis, Mo., USA)
1% penicillin/streptomycin (Thermo/Fisher Scientific, Waltham, Mass., USA)

The chemically-defined lipid concentrate contains lipids arachidonic acid 2.0 mg/L, cholesterol 220 mg/L, DL-alpha-tocopherol acetate 70 mg/L, linoleic acid 10 mg/L, linolenic acid 10 mg/L, myristic acid 10 mg/L, oleic acid 10 mg/L, palmitic acid 10 mg/L, palmitoleic acid 10 mg/L, and stearic acid 10 mg/L.

FIG. 3 shows images obtained of the AECs after 0 h (propagation media removed, washed and SFM added and immediately imaged) and 24 h in each of the three types of media. Specifically, panels 3A and 3B show the results with DMEM, panels 3C and 3D show the results with SFM2, and panels 3E and 3F show the results with SFM1. A comparison of panel 3B with panels 3D and 3F shows that the cells appeared relatively more spindly, taken on more of a fibroblast-like morphology, in the DMEM media (FIG. 3B), whereas the cells incubated for 24 h in both SFM1 and SFM2 maintained their epithelial morphology. Based on these results, serum-free DMEM media was not used for the future culture of AEC cells.

Example 2

Production of Amniotic Cell Conditioned Media

Amniotic cell conditioned media (ACCM) was produced as described below.

Materials. The AECs used to produce ACCM were derived from placental tissue and propagated as described above in Example 1. The AFCs used to produce ACCM were derived from amniotic fluid and propagated as described above in Example 1.

Methods. ACCM was produced as illustrated in the flow diagram FIG. 4. Each of the AECs and AFCs were cultured for expansion using standard procedures in AEC Propagation media or AFC propagation media, respectively. Each of the two cell types were passaged twice as shown in steps 402, 404, 406, and 408. At this point, the AECs were mitotically inactivated to arrest cell division by treating with mitomycin C dissolved in propagation media at 4 ug/ml for 2 h as shown in step 410. The AECs were then immediately trypsinized, counted, and plated and the AECs were allowed to attach to the collagen-coated culture dish overnight in propagation media (step 410). The AFCs were detached, counted and plated on top of the AEC feeder layer and allowed to attach for 6 h in AEC propagation media (step 412). Following attachment, the co-culture of the AFCs and AECs ("co-AC") was thoroughly washed with PBS and serum free media (SFM) was added (step 414). The co-AC cells were cultured for 24 h, at which point the conditioned media was collected (step 416).

The amniotic cell conditioned medium (ACCM) from the co-AC cells in the method described above was analyzed as follows. FIG. 5 shows analysis of the ACCM by SDS-PAGE in which the two different types of serum free media described in Example 1 above (SFM1 and SFM2) were tested in the method at step 414. In the SDS-PAGE gel shown in FIG. 5, 1 µg total protein was loaded in lanes (from left to right) consisting of bovine serum albumin (BSA; control to identify albumin), DMEM/F12+10% fetal bovine serum (D/F12+S), unconditioned serum-free media 1 (SFM1; unc), co-AC conditioned SFM1 (SFM1; co-AC), AEC conditioned SFM1 (SFM1; AEC), AFC conditioned SFM1 (SFM1; AFC), unconditioned serum-free media 2 (SFM2; unc), co-AC conditioned SFM2 (SFM2; co-AC), AEC conditioned SFM2 (SFM2; AEC), and AFC conditioned SFM2 (SFM2; AFC), and electrophoresed on 10% SDS-polyacrylamide gel then silver stained and scanned on a Li-Cor Odyssey CLx. The signal intensity calculated per lane is shown as "signal/microgram" at the bottom of the gel determined by generating a region of interest consisting of each lane and determining signal counts within using ImageStudio software program. Molecular weight in kilodaltons (kDa) is shown on the left; ND denotes no signal detected above background; all conditioned medias analyzed were generated by 24 h culture and unconditioned medias by 24 h incubation in a well of the same culture plate but minus cells.

As can be seen in FIG. 5, the co-culture of the AECs and AFCs (co-AC) in the defined media, SFM1, resulted in increased total protein secretion and increased protein complexity (e.g., the same amount of total protein (1 µg) is added in each lane, but the co-AC conditioned media shows both different bands present and an increased signal intensity relative to AECs or AFCs alone). Surprisingly, the co-culture of the AECs and AFCs in the SFM2 media shows no apparent protein secretion at all compared to unconditioned media. These data illustrate a synergistic effect of the co-culture of the AECs and AFCs in the SFM1 media that can yield a conditioned media having both increased protein concentration and complexity.

The amniotic cell conditioned medium (ACCM) from the co-culture of the AECs and AFCs in the SFM1 media in the method described above was further analyzed by Bradford assay and LC-MS/MS and the data are shown in FIG. 6. Unconditioned SFM1 media (SFM1), the co-AC conditioned SFM1 (co-AC), the AEC conditioned SFM1 (AEC), and the AFC conditioned SFM1 (AFC) were measured for total protein concentration using the Bradford method or the proteome analyzed by liquid chromatography-tandem mass spectrometry (LC-MS/MS) to determine unique proteins present in each sample and the percent of proteins per sample relative to all proteins identified in each of the 4 groups assayed. As can be seen in FIG. 6, the co-culture of the AECs and AFCs in the SFM1 media according to the method described above resulted in the highest total protein concentration by Bradford assay. Using the LC-MS/MS method a higher number of proteins (by identity) is observed compared to AECs or AFCs alone. The viable cell results from the trypan blue exclusion assay show that the AFC alone cell count is the same as the co-AC cell count, indicating that the higher protein concentration and increased number of distinct protein identities results from the same number of cells per well. These data show the synergistic effect of the co-culture of the AECs and AFCs in the SFM1 media that can yield a conditioned media having both increased protein concentration and complexity.

FIG. 7 is a Venn diagram of the LC-MS/MS data shown in FIG. 6 showing that the co-culture of the AECs and AFCs in the SFM1 media yields 84 unique proteins by identity not observed in either the AEC- or AFC alone conditioned SFM1. This result illustrates the synergistic effect of the co-culture of the AECs and AFCs in the SFM1 media that can yield a conditioned media with increased protein complexity.

FIG. 8 shows, by quantitative analysis, the number and percentage of proteins identified by LC-MS/MS in the conditioned SFM1 from the co-culture of the AECs and AFCs according to the method described above. The data in FIG. 8 show that the co-culture of the AECs and AFCs yielded quantitatively higher levels of proteins than in either AECs only, AFCs only, or the sum of AECs and AFCs only. The first row in FIG. 8 is normalized total spectral counts for the co-culture of the AECs and AFCs in SFM1 that is greater than zero (co-AC>0); the second row in FIG. 8 is co-AC after subtracting the background contribution of unconditioned media (co-AC>BG), the third row in FIG. 8 is co-AC protein levels after subtracting background plus AEC alone-conditioned SFM1 protein levels (co-AC>(BG+AEC)), the fourth row in FIG. 8 is co-AC protein levels after subtracting background plus AFC alone-conditioned SFM1 protein levels (co-AC>(BG+AFC)), and the fifth row in FIG. 8 is co-AC protein levels after subtracting background plus AEC alone-conditioned SFM1 plus AFC alone-conditioned SFM1 protein levels (co-AC>(BG+AEC+AFC)). The results in FIG. 8 show that the quantity of 225 of the identified proteins (27.3% of the total) are present at a higher level in the conditioned media from co-culture of AECs and AFCs than the additive level of AEC alone-conditioned SFM1 plus AFC alone-conditioned SFM1. These data illustrate, using a quantitative analysis of the proteome, the synergistic effect of the co-culture of the AECs and AFCs in the SFM1 media that can yield a conditioned media with increased protein concentration and complexity, and rule-out a simply additive effect of AFC and AEC conditioning alone.

Gene ontology (GO) term analysis was performed to identify significantly enriched biological pathways represented within the proteome of conditioned SFM1 from the co-culture of the AECs and AFCs according to the method described above. The results are shown in FIG. 9. LC-MS/MS data from the conditioned SFM1 was compared to unconditioned SFM1 LC-MS/MS data (input as background data set) to derive enriched ($p \leq 0.05$) GO terms. Selected GO terms are shown on the Y-axis and p-values are plotted on the X-axis as 1eX with X being the value shown on the X-axis.

Example 3

Effects of ACCM on Liver

Cell-based assays are performed to test ACCM in promoting liver cell homeostasis. Assays are performed to test hepatocyte and cholangiocyte growth in ACCM vs. unconditioned media. Assays are performed to determine the role of ACCM in the prevention of cell death induced by reactive oxygen species (ROS) by culturing cells in ACCM as compared to cells cultured in unconditioned media. The capability of ACCM to reduce stellate cell activation (induces liver fibrosis long-term) is tested by comparing cells cultured in ACCM to those cultured in unconditioned media.

Example 4

Effects of ACCM in Promotion of Wound Healing

Cell-based assays are performed to test ACCM in promoting wound healing by determining fibroblast and myoblast migration in response to ACCM vs. unconditioned media (scratch assay and transwell insert migration/matrigel invasion assay).

Any patents or publications mentioned in this specification are indicative of the levels of those skilled in the art to which the present disclosure pertains. These patents and publications are herein incorporated by reference in their entirety to the same extent as if each individual publication was specifically and individually indicated to be incorporated by reference.

One skilled in the art will readily appreciate that the present disclosure is well adapted to carry out the objects and obtain the ends and advantages mentioned, as well as those inherent therein. The present Examples along with the methods described herein are presently representative of preferred embodiments, are exemplary, and are not intended as limitations on the scope of the invention. Changes therein and other uses will occur to those skilled in the art which are encompassed within the spirit of the present disclosure as defined by the scope of the claims.

That which is claimed:

1. A topical composition comprising a composition having components of amniotic fluid derived from a co-culture of amniotic epithelial cells (AECs) and amniotic fluid cells (AFCs) and a carrier, wherein the composition having components of amniotic fluid is a conditioned supernatant that comprises both increased protein concentration and increased protein complexity compared to a control culture of AECs alone or AFCs alone, and is produced by a process comprising:
  (a) transferring amniotic epithelial cells (AECs) and amniotic fluid cells (AFCs) to a cell culture system and co-culturing the AECs and AFCs in a defined serum free media consisting of a base media, wherein the base media is 50% Iscove's Modified Dulbecco's Media (IMDM) and 50% F12 media; monothioglycerol (450 µM), 1 mg/ml polyvinyl alcohol, 1% penicillin/streptomycin and 1% chemically defined lipid concentrate, wherein the chemically defined lipid concentrate contains 2.0 mg/L arachidonic acid, 220 mg/L cholesterol, 70 mg/L DL-alpha-tocopherol acetate, 10 mg/L linoleic acid, 10 mg/L linolenic acid, 10 mg/L myristic acid, 10 mg/L oleic acid, 10 mg/L palmitic acid, 10 mg/L palmitoleic acid, and 10 mg/L stearic acid; and where a synergistic effect of the co-culture of the AECs and AFCs in the base media results in increased protein concentration and complexity when compared to a control culture of AECs alone or AFCs alone;
  (b) separating the AECs and AFCs co-cultured in (a) from the culture medium to obtain a conditioned supernatant;
  (c) removing large molecules and other cell debris from the conditioned supernatant of (b);
  (d) ensuring the sterility of the conditioned supernatant of (c); and
  (e) concentrating the sterile conditioned supernatant of (d) to produce a concentrated, sterile conditioned supernatant and determining total protein concentration, protein complexity or both;
  wherein the composition comprising components of amniotic fluid is the concentrated, sterile conditioned supernatant that comprises both increased protein concentration and increased protein complexity compared to the control culture of AECs alone or AFCs alone.

2. The topical composition of claim 1, wherein a majority of the co-cultured AECs and AFCs are amniotic stem cells.

3. The topical composition of claim 1, wherein
  (a) the AECs are attached to a surface of the cell culture system and the AFCs are deposited on top of the AECs; or
  (b) the AECs are mitotically inactivated prior to transferring to the cell culture system; or
  (c) the AECs and AFCs are expanded prior to transferring to the cell culture system by passaging the AECs and AFCs one, two or three times; or
  (d) the AECs and AFCs are derived from a mammalian tissue without having been previously frozen.

4. The topical composition of claim 1, wherein the AECs are mitotically inactivated prior to transferring to the cell culture system and/or the AECs and AFCs are expanded prior to transferring to the cell culture system by passaging the AECs and AFCs one, two or three or more times.

5. The topical composition of claim 1, wherein the AECs and AFCs are derived from a mammalian tissue without having been previously frozen, optionally wherein the mammalian tissue is a human tissue.

6. The topical composition of claim 1, further comprising from about 0.1 to about 20% of a moisturizing agent, a vitamin B3 compound, an antioxidant, or a combination thereof.

7. The topical composition of claim 6, wherein
  (a) the moisturizing agent comprises one or more of panthenol, pantothenic acid derivatives, glycerin, glycerol, dimethicone, petrolatum, hyaluronic acid, or ceramides, and mixtures thereof; or
  (b) the vitamin B3 compound comprises tocopherol nicotinate; or
  (c) the anti-oxidant comprises one or a combination of tocopherol or esters of tocopherol; or
  (d) the composition is in the form of a liquid, lotion, cream, gel, foam, mousse, spray, paste, powder, or solid.

8. The topical composition of claim 1, wherein the composition is effective for regulating a skin condition.

9. The topical composition of claim 8, wherein regulating a skin condition includes one or more of inducing increased skin integrity by cell renewal; enhancing water content or moisture of skin; reducing trans epidermal water loss, skin flaking, and scaling; improving skin thickness; enhancing skin tensile properties; reducing the appearance of dermal fine lines and wrinkles; improving skin texture; reducing skin pores size; enhancing skin smoothness; improving skin age spots; improving skin tone; or improving the appearance of scars and skin abrasions.

10. A method for making a composition having components of amniotic fluid, the method comprising:
  (a) transferring amniotic epithelial cells (AECs) and amniotic fluid cells (AFCs) to a cell culture system and culturing the AECs and AFCs in a defined medium essentially free of serum consisting of a base media; wherein the base media is 50% Iscove's Modified Dulbecco's Media (IMDM) and 50% F12 media; monothioglycerol (450 µM), 1 mg/ml polyvinyl alcohol, 1% penicillin/streptomycin and 1% chemically defined lipid concentrate, wherein the chemically defined lipid concentrate contains 2.0 mg/L arachidonic acid, 220 mg/L cholesterol, 70 mg/L DL-alpha-tocopherol acetate, 10 mg/L linoleic acid, 10 mg/L linolenic acid, 10 mg/L myristic acid, 10 mg/L oleic acid, 10 mg/L palmitic acid, 10 mg/L palmitoleic acid, and 10 mg/L stearic acid; and where a synergistic effect of the co-culture of the AECs and AFCs in the base media results in increased protein concentration and complexity when compared to a control culture of AECs alone or AFCs alone;
  (b) separating the co-cultured AECs and AFCs from the culture medium of (a) to obtain a conditioned supernatant;
  (c) removing large molecules and other cell debris from the conditioned supernatant of (b);
  (d) ensuring the sterility of the conditioned supernatant of (c); and
  (e) concentrating the sterile conditioned supernatant of (d) to produce a concentrated, sterile conditioned supernatant and determining total protein concentration, protein complexity or both;
  wherein the composition comprising components of amniotic fluid is the concentrated, sterile conditioned supernatant that comprises both increased protein concentration and increased protein complexity compared to the control culture of AECs alone or AFCs alone.

11. The method of claim 10, wherein
  (a) the AECs are attached to a surface of the culture system and the AFCs are deposited on top of the ABCs; or
  (b) the AECs are mitotically inactivated prior to transferring to the cell culture system; or (c) the AECs and AFCs are expanded prior to transferring to the cell culture system by passaging the AECs and AFCs one, two or three times; or (d) the AECs and AFCs are derived from a mammalian tissue without having been previously frozen.

12. The method of claim 11, wherein the mammalian tissue is a human tissue.

13. A method for making a composition having components of amniotic fluid derived from a co-culture of amniotic epithelial cells (AECs) and amniotic fluid cells (AFCs) and a carrier, the method comprising:

(a) transferring amniotic fluid cells (AFCs) and amniotic epithelial cells (AECs) to a cell culture system and co-culturing the AECs and AFCs in a defined medium essentially free of serum consisting of a base media to a predetermined target total protein concentration in the culture medium, wherein the base media is 50% Iscove's Modified Dulbecco's Media (IMDM) and 50% F12 media; monothioglycerol (450 µM), 1 mg/ml polyvinyl alcohol, 1% penicillin/streptomycin and 1% chemically defined lipid concentrate, wherein the chemically defined lipid concentrate contains 2.0 mg/L arachidonic acid, 220 mg/L cholesterol, 70 mg/L DL-alpha-tocopherol acetate, 10 mg/L linoleic acid, 10 mg/L linolenic acid, 10 mg/L myristic acid, 10 mg/L oleic acid, 10 mg/L palmitic acid, 10 mg/L palmitoleic acid, and 10 mg/L stearic acid; and where a synergistic effect of the co-culture of the AECs and AFCs in the base media results in increased protein concentration and complexity when compared to a control culture of AECs alone or AFCs alone;

(b) separating the co-cultured AECs and AFCs of (a) from the culture medium to obtain a conditioned supernatant;

(c) removing large molecules and other cell debris from the conditioned supernatant of (b); and (d) ensuring the sterility of the conditioned supernatant of (c); and (e) concentrating the sterile conditioned supernatant of (d) to produce a concentrated, sterile conditioned supernatant and determining total protein concentration, protein complexity or both;

wherein the composition comprising components of amniotic fluid is the concentrated, sterile conditioned supernatant that comprises both increased protein concentration and increased protein complexity compared to the control culture of AECs alone or AFCs alone.

14. The method of claim 13, wherein the amniotic epithelial cells (AECs) and amniotic fluid cells (AFCs) are derived from a mammalian tissue without having been previously frozen, optionally wherein the mammalian tissue is a human tissue.

15. A method for preservation of an organ, the method comprising surrounding the organ in a composition having components of amniotic fluid according to claim 1, wherein the organ is preserved in the composition, wherein the organ is intended for use as a transplant organ.

16. A method for regulating a human skin condition which comprises applying to human skin at least once a day over at least seven days or at least twice a day over at least fourteen days a topical composition according to claim 1.

17. A method for tissue repair, the method comprising one of putting on, embedding into, filling, or injecting a tissue with a composition having components of amniotic fluid produced by a process comprising:

(a) transferring amniotic epithelial cells (AECs) and amniotic fluid cells (AFCs) to a cell culture system and culturing the AECs and AFCs in a defined medium essentially free of serum consisting of a base media, wherein the base media is 50% Iscove's Modified Dulbecco's Media (IMDM) and 50% F12 media; monothioglycerol (450 µM), 1 mg/ml polyvinyl alcohol, 1% penicillin/streptomycin and 1% chemically defined lipid concentrate, wherein the chemically defined lipid concentrate contains 2.0 mg/L arachidonic acid, 220 mg/L cholesterol, 70 mg/L DL-alpha-tocopherol acetate, 10 mg/L linoleic acid, 10 mg/L linolenic acid, 10 mg/L myristic acid, 10 mg/L oleic acid, 10 mg/L palmitic acid, 10 mg/L palmitoleic acid, and 10 mg/L stearic acid; and where a synergistic effect of the co-culture of the AECs and AFCs in the base media results in increased protein concentration and complexity when compared to a control culture of AECs alone or AFCs alone;

(b) separating the co-cultured AECs and AFCs in (a) from the culture medium to obtain a conditioned supernatant;

(c) removing large molecules and other cell debris from the conditioned supernatant of (b); and (d) ensuring the sterility of the conditioned supernatant of (c);

and (e) concentrating the sterile conditioned supernatant to produce a concentrated, sterile conditioned supernatant and determining total protein concentration, protein complexity or both;

wherein the composition comprising components of amniotic fluid is the concentrated, sterile conditioned supernatant that comprises both increased protein concentration and increased protein complexity compared to the control culture of AECs alone or AFCs alone, and wherein the tissue is repaired by the putting on, embedding into, filling, or injecting of the tissue with the composition.

18. The method of claim 17, wherein the tissue comprises dermal, scar, cartilage, tendon, ligament, muscle, bone, periodontal, cardiovascular, hematologic, pulmonary, urologic, ophthalmic, liver, or kidney tissue, or combinations thereof and the tissue repair is selected from one or a combination of promotion of cell/tissue homeostasis, reduction of inflammation, wounds and burns, infection treatment, sepsis treatment, repair of scarring, post-operative scarring, joint repair, rheumatoid arthritis treatment, psoriatic arthritis treatment, gout treatment, bursitis treatment, joint replacement surgery, tendon repair, tendinitis treatment, rotator cuff repair, muscle repair, repair, osteoarthritis treatment, arthritis treatment, male urologic dysfunction treatment, Critical Limb Ischemia treatment, Intermittent Claudication treatment, Buerger's Disease treatment, Ischemic Heart Disease treatment, Diastolic Heart Failure treatment, bronchopulmonary dysplasia, chronic obstructive pulmonary disease, ophthalmic disorders, and reversal of aging.

19. The method of claim 17, wherein (a) the composition is a dermal, cartilage, or bone gel; or (b) the AECs are attached to a surface of the culture system and the AFCs are deposited on top of the ABCs; or (c) the AECs are mitotically inactivated prior to transferring to the cell culture system; or (d) the AECs and AFCs are expanded prior to transferring to the cell culture system by passaging the AECs and AFCs one, two or three times; or (e) the AECs and AFCs are derived from a mammalian tissue without having been previously frozen.

20. The method of claim 19, wherein the mammalian tissue is a human tissue.

\* \* \* \* \*